United States Patent
Garde et al.

(10) Patent No.: US 11,690,713 B2
(45) Date of Patent: Jul. 4, 2023

(54) ANTI-PARAVALVULAR LEAKAGE COMPONENT FOR A TRANSCATHETER VALVE PROSTHESIS

(71) Applicant: Medtronic CV Luxembourg S.A.R.L., Luxembourg (LU)

(72) Inventors: Kshitija Garde, Irvine, CA (US); Joel Racchini, Minnesota, MN (US); Paul Rothstein, Elk River, MN (US); Jeffrey Sandstrom, Scandia, MN (US)

(73) Assignee: Medtronic CV Luxembourg S.A.R.L., Luxembourg (LU)

( * ) Notice: Subject to any disclaimer, the term of this patent is extended or adjusted under 35 U.S.C. 154(b) by 394 days.

(21) Appl. No.: 16/891,301

(22) Filed: Jun. 3, 2020

(65) Prior Publication Data

US 2020/0289262 A1 Sep. 17, 2020

Related U.S. Application Data

(60) Division of application No. 15/494,923, filed on Apr. 24, 2017, now Pat. No. 10,702,379, which is a
(Continued)

(51) Int. Cl.
*A61F 2/24* (2006.01)

(52) U.S. Cl.
CPC .......... *A61F 2/2418* (2013.01); *A61F 2/2409* (2013.01); *A61F 2220/005* (2013.01);
(Continued)

(58) Field of Classification Search
CPC ........ A61F 2/2418; A61F 2/2409; A61F 2/24; A61F 2/848
See application file for complete search history.

(56) References Cited

U.S. PATENT DOCUMENTS

| 5,571,175 A | 11/1996 | Vanney et al. |
| 7,276,078 B2 | 10/2007 | Spenser et al. |

(Continued)

FOREIGN PATENT DOCUMENTS

| EP | 0537487 A1 | 4/1993 |
| WO | 2009/094501 A1 | 7/2009 |

(Continued)

*Primary Examiner* — Seema Mathew
(74) *Attorney, Agent, or Firm* — Medler Ferro Woodhouse & Mills PLLC

(57) ABSTRACT

A transcatheter valve prosthesis includes an expandable tubular stent, a prosthetic valve within the stent, and an anti-paravalvular leakage component coupled to and encircling the tubular stent. The anti-paravalvular leakage component includes a radially-compressible annular scaffold, which is a sinusoidal patterned ring of self-expanding material, and an impermeable membrane extending over the annular scaffold. The anti-paravalvular leakage component has an expanded configuration in which at least segments of the annular scaffold curve radially away from the tubular stent. Alternatively, the anti-paravalvular leakage component includes a plurality of self-expanding segments and an annular sealing element coupled to inner surfaces of the segments. The anti-paravalvular leakage component has an expanded configuration in which the segments curve radially away from the tubular stent and the annular sealing element is positioned between an outer surface of the tubular stent and inner surfaces of the segments. The segments may be orthogonal or oblique to the outer surface of the tubular stent.

19 Claims, 24 Drawing Sheets

Related U.S. Application Data continuation of application No. 14/242,347, filed on Apr. 1, 2014, now Pat. No. 9,675,451, which is a continuation-in-part of application No. 13/757,380, filed on Feb. 1, 2013, now Pat. No. 10,413,401.

(52) U.S. Cl.
CPC . *A61F 2220/0075* (2013.01); *A61F 2230/008* (2013.01); *A61F 2230/0013* (2013.01); *A61F 2230/0017* (2013.01); *A61F 2230/0069* (2013.01); *A61F 2230/0078* (2013.01); *A61F 2250/0069* (2013.01)

(56) References Cited

U.S. PATENT DOCUMENTS

| | | | |
|---|---|---|---|
| 7,331,991 B2 | 2/2008 | Kheradvar et al. | |
| 7,628,805 B2 | 12/2009 | Spenser et al. | |
| 7,708,775 B2 | 5/2010 | Rowe et al. | |
| 7,780,725 B2 | 8/2010 | Haug et al. | |
| 8,002,825 B2 | 8/2011 | Letac et al. | |
| 8,182,528 B2 | 5/2012 | Salahieh et al. | |
| 8,231,670 B2 | 7/2012 | Salahieh et al. | |
| 8,449,599 B2 | 5/2013 | Chau et al. | |
| 8,603,160 B2 | 12/2013 | Salahieh et al. | |
| 8,623,078 B2 | 1/2014 | Salahieh et al. | |
| 8,628,566 B2 | 1/2014 | Eberhardt et al. | |
| 8,641,757 B2 | 2/2014 | Pintor et al. | |
| 8,668,733 B2 | 3/2014 | Haug et al. | |
| 8,673,000 B2* | 3/2014 | Tabor | A61F 2/013 623/1.24 |
| 8,734,484 B2 | 5/2014 | Ahlberg et al. | |
| 8,795,357 B2 | 8/2014 | Yohanan et al. | |
| 8,801,706 B2 | 8/2014 | Rothstein et al. | |
| 8,802,356 B2 | 8/2014 | Yun et al. | |
| 9,132,007 B2* | 9/2015 | Menk | A61F 2/246 |
| 9,675,451 B2* | 6/2017 | Garde | A61F 2/2409 |
| 9,681,951 B2* | 6/2017 | Ratz | A61F 2/2418 |
| 9,974,669 B2 | 5/2018 | Quadri | |
| 10,166,097 B2 | 1/2019 | Quadri et al. | |
| 10,869,756 B2* | 12/2020 | Al-Jilaihawi | A61F 2/2436 |
| 10,888,420 B2* | 1/2021 | Bateman | A61F 2/2439 |
| 11,571,296 B2* | 2/2023 | Kaleta | A61F 2/2418 |
| 2003/0199963 A1 | 10/2003 | Tower et al. | |
| 2003/0199971 A1 | 10/2003 | Tower et al. | |
| 2004/0030381 A1 | 2/2004 | Shu | |
| 2004/0111111 A1 | 6/2004 | Lin | |
| 2004/0122514 A1 | 6/2004 | Fogarty et al. | |
| 2005/0137695 A1* | 6/2005 | Salahieh | A61F 2/2439 623/2.11 |
| 2006/0004442 A1 | 1/2006 | Spenser et al. | |
| 2006/0271172 A1 | 11/2006 | Tehrani | |
| 2007/0173929 A1 | 7/2007 | Boucher et al. | |
| 2007/0270944 A1 | 11/2007 | Berghein et al. | |
| 2007/0293944 A1 | 12/2007 | Spenser et al. | |
| 2008/0071361 A1 | 3/2008 | Tuval et al. | |
| 2008/0243245 A1 | 10/2008 | Thambar et al. | |
| 2009/0099653 A1* | 4/2009 | Suri | A61F 2/2418 623/2.11 |
| 2009/0112311 A1 | 4/2009 | Miles et al. | |
| 2009/0192591 A1 | 7/2009 | Ryan et al. | |
| 2010/0036479 A1 | 2/2010 | Hill et al. | |
| 2010/0168844 A1 | 7/2010 | Toomes et al. | |
| 2010/0198238 A1 | 8/2010 | Sorajja | |
| 2010/0277413 A1 | 11/2010 | Wang et al. | |
| 2010/0280589 A1 | 11/2010 | Styrc | |
| 2010/0298931 A1* | 11/2010 | Quadri | A61F 2/243 623/2.11 |
| 2011/0054466 A1 | 3/2011 | Rothstein et al. | |
| 2011/0098802 A1* | 4/2011 | Braido | A61F 2/2436 623/2.11 |
| 2011/0137397 A1 | 6/2011 | Chau et al. | |
| 2011/0172765 A1 | 7/2011 | Nguyen et al. | |
| 2011/0245911 A1 | 10/2011 | Quill et al. | |
| 2011/0257721 A1 | 10/2011 | Tabor | |
| 2011/0264196 A1 | 10/2011 | Savage et al. | |
| 2011/0264206 A1* | 10/2011 | Tabor | A61F 2/2418 623/2.12 |
| 2012/0022633 A1 | 1/2012 | Olson et al. | |
| 2012/0041549 A1 | 2/2012 | Salahieh et al. | |
| 2012/0041550 A1 | 2/2012 | Salahieh et al. | |
| 2012/0053682 A1 | 3/2012 | Kovalsky et al. | |
| 2013/0190857 A1 | 7/2013 | Mitra et al. | |
| 2013/0190862 A1 | 7/2013 | Pintor et al. | |
| 2013/0197622 A1* | 8/2013 | Mitra | A61F 2/2418 623/1.15 |
| 2013/0304200 A1 | 11/2013 | McLean et al. | |
| 2013/0310928 A1 | 11/2013 | Morriss et al. | |
| 2013/0317603 A1 | 11/2013 | McLean et al. | |
| 2013/0331929 A1* | 12/2013 | Mitra | A61F 2/2418 623/2.11 |
| 2014/0046426 A1 | 2/2014 | Kovalsky | |
| 2014/0052237 A1 | 2/2014 | Lane et al. | |
| 2014/0114402 A1* | 4/2014 | Ahlberg | A61F 2/2418 623/2.11 |
| 2014/0114406 A1 | 4/2014 | Salahieh et al. | |
| 2014/0194975 A1 | 7/2014 | Quill et al. | |
| 2014/0194981 A1 | 7/2014 | Menk et al. | |
| 2014/0222144 A1* | 8/2014 | Eberhardt | A61F 2/2409 623/2.38 |
| 2014/0236287 A1 | 8/2014 | Clague et al. | |
| 2014/0243966 A1 | 8/2014 | Garde et al. | |
| 2014/0243969 A1 | 8/2014 | Venkatasubramanian et al. | |
| 2014/0257475 A1 | 9/2014 | Gross et al. | |
| 2014/0277388 A1 | 9/2014 | Skemp | |
| 2014/0277417 A1 | 9/2014 | Schraut et al. | |
| 2014/0277419 A1* | 9/2014 | Garde | A61F 2/2403 623/2.18 |
| 2014/0277423 A1 | 9/2014 | Alkhatib et al. | |
| 2014/0277424 A1 | 9/2014 | Oslund | |
| 2014/0277425 A1 | 9/2014 | Dakin | |
| 2014/0277426 A1 | 9/2014 | Dakin et al. | |
| 2014/0277428 A1 | 9/2014 | Skemp et al. | |
| 2014/0296969 A1 | 10/2014 | Tegels et al. | |
| 2014/0296975 A1 | 10/2014 | Tegels et al. | |
| 2014/0324164 A1 | 10/2014 | Gross et al. | |
| 2015/0122687 A1 | 5/2015 | Zeng et al. | |
| 2015/0142103 A1 | 5/2015 | Mdlund | |
| 2015/0289973 A1* | 10/2015 | Braido | A61F 2/2412 623/2.17 |
| 2015/0305860 A1 | 10/2015 | Wang et al. | |
| 2015/0327995 A1* | 11/2015 | Morin | A61F 2/2436 623/2.17 |
| 2016/0030171 A1 | 2/2016 | Quijano et al. | |
| 2016/0194425 A1 | 7/2016 | Mitra et al. | |
| 2016/0270910 A1* | 9/2016 | Birmingham | A61F 2/844 |
| 2016/0324635 A1 | 11/2016 | Vidlund et al. | |
| 2017/0086973 A1 | 3/2017 | Zeng et al. | |
| 2018/0325662 A1 | 11/2018 | Modine | |
| 2021/0196459 A1* | 7/2021 | Marchand | A61F 2/2427 |

FOREIGN PATENT DOCUMENTS

| | | |
|---|---|---|
| WO | 2011/051043 A1 | 5/2011 |
| WO | 2013/033791 A1 | 3/2013 |
| WO | 2013/059747 A1 | 4/2013 |
| WO | 2014072439 A1 | 5/2014 |

* cited by examiner

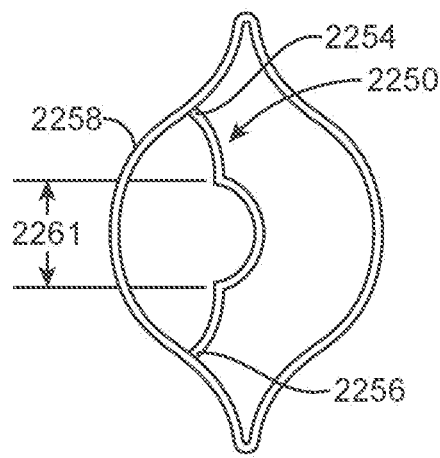 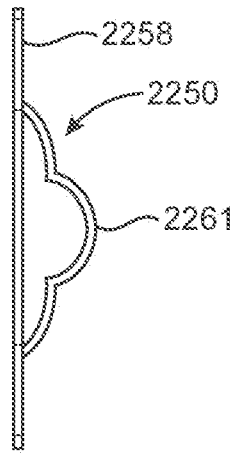
FIG. 22A  FIG. 22B
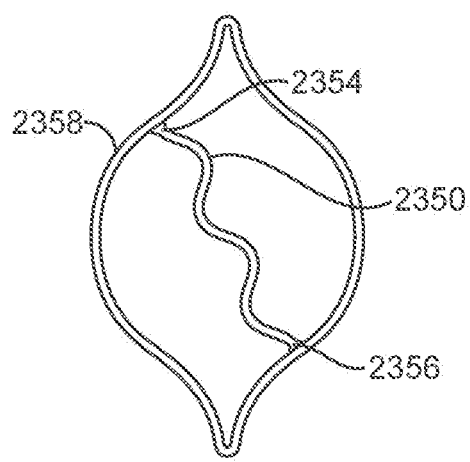 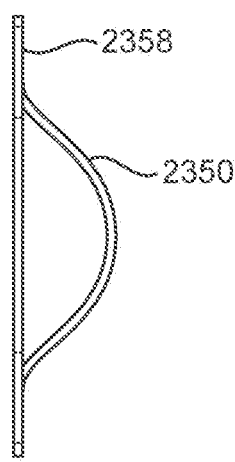
FIG. 23A  FIG. 23B

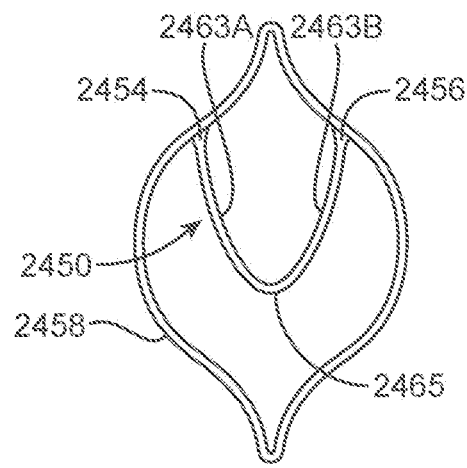 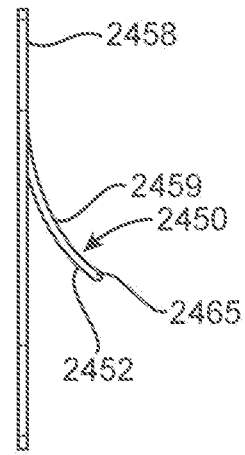
FIG. 24A  FIG. 24B
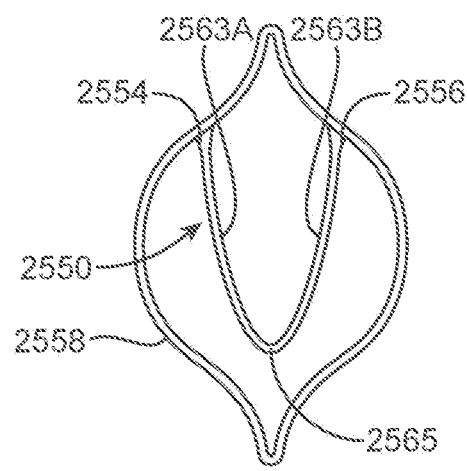 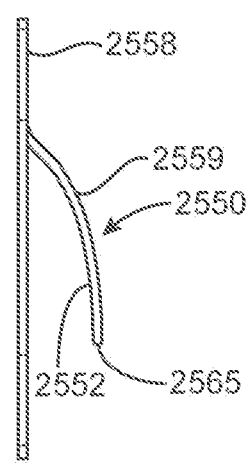
FIG. 25A  FIG. 25B

ANTI-PARAVALVULAR LEAKAGE COMPONENT FOR A TRANSCATHETER VALVE PROSTHESIS

CROSS-REFERENCE TO RELATED APPLICATIONS

This application is a divisional of U.S. application Ser. No. 15/494,923, filed Apr. 24, 2017, which is a continuation of U.S. application Ser. No. 14/242,347, filed Apr. 1, 2014, now U.S. Pat. No. 9,675,451, which is a continuation-in-part of U.S. application Ser. No. 13/757,380, filed Feb. 1, 2013, now U.S. Pat. No. 10,413,401, the disclosures of which are each herein incorporated by reference in their entirety.

FIELD OF THE INVENTION

The present invention relates to transcatheter valve prostheses and methods of preventing paravalvular leakage. More specifically, the present invention relates to an anti-paravalvular leakage component integrated on an outer surface of a transcatheter valve prosthesis to seal gaps between a support frame of the prosthesis and native valve tissue.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart, ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the mitral valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to anti-paravalvular leakage components coupled to an outer surface of the valve prosthesis to seal gaps between the valve prosthesis and native valve tissue.

BRIEF SUMMARY OF THE INVENTION

Embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a plurality of self-expanding segments and an annular sealing element attached to the segments. A first end and a second end of each segment is attached to the outer surface of the tubular stent at spaced apart first and second attachment points, respectively. The anti-paravalvular leakage component has an expanded configuration in which the segments curve radially away from the outer surface of the tubular stent and are oblique to the outer surface of the tubular stent such that a plane defined by each segment is non-perpendicular with respect to a tangential plane of the tubular stent taken through the first and second attachments points.

According to other embodiments hereof, embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a plurality of self-expanding segments and an annular sealing element attached to the segments. A first end and a second end of each segment is attached to the outer surface of the tubular stent at spaced apart first and second attachment points, respectively. The anti-paravalvular leakage component has an expanded configuration in which the segments curve radially away from the outer surface of the tubular stent, and the flexibility of the anti-paravalvular leakage component at the plurality of segments varies around the circumference of the tubular stent when the anti-paravalvular leakage component is in the expanded configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 13 is side view of the heart valve prosthesis of FIG. 12 in a deployed or expanded configuration, with the annular sealing element removed for clarity.

FIG. 14 is a side view of the heart valve prosthesis of FIG. 13 in a compressed or delivery configuration.

FIGS. 22A-22B illustrate front and side views, respectively, of one or more diamond-shaped openings of a stent, wherein an oblique self-expanding segment according to another embodiment hereof is coupled to the stent.

FIGS. 23A-23B illustrate front and side views, respectively, of one or more diamond-shaped openings of a stent, wherein an oblique self-expanding segment according to another embodiment hereof is coupled to the stent.

FIGS. 24A-24B illustrate front and side views, respectively, of one or more diamond-shaped openings of a stent, wherein an oblique self-expanding segment according to another embodiment hereof is coupled to the stem.

FIGS. 25A-25B illustrate front and side views, respectively, of one or more diamond-shaped openings of a stent, wherein an oblique self-expanding segment according to another embodiment hereof is coupled to the stent.

DETAILED DESCRIPTION OF THE INVENTION

Specific embodiments of the present invention are now described with reference to the figures, wherein like reference numbers indicate identical or functionally similar elements. If utilized herein, the terms "distal" or "distally" refer to a position or in a direction away from the heart and the terms "proximal" and "proximally" refer to a position near or in a direction toward the heart. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
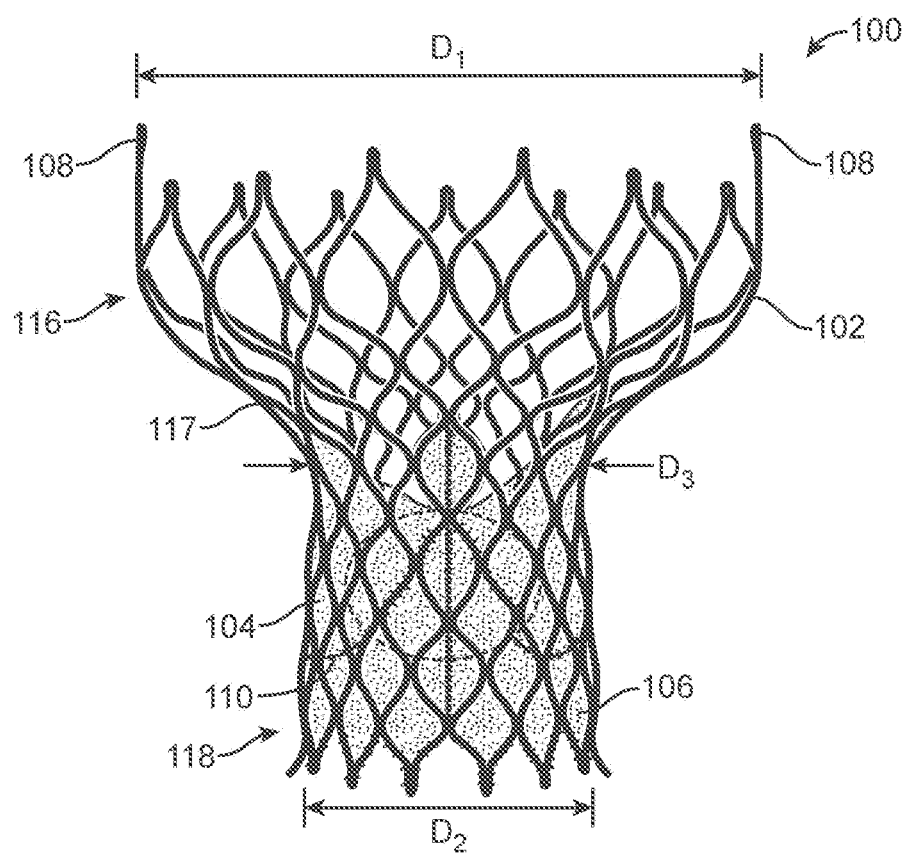
FIG. 1 is a side view illustration of an exemplary transcatheter heart valve prosthesis for use in embodiments hereof.

FIG. 1 depicts an exemplary transcatheter heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 includes an expandable stent or frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as Nitinol, or a polymer, such as any of the polymers disclosed in U.S. Pat. Appl. Pub. No. 2004/0111111 to Lin, which is incorporated by reference herein in its entirety. Alternatively, heart valve prosthesis 100 may be balloon-expandable as would be understood by one of ordinary skill in the art.

Figure 1A:
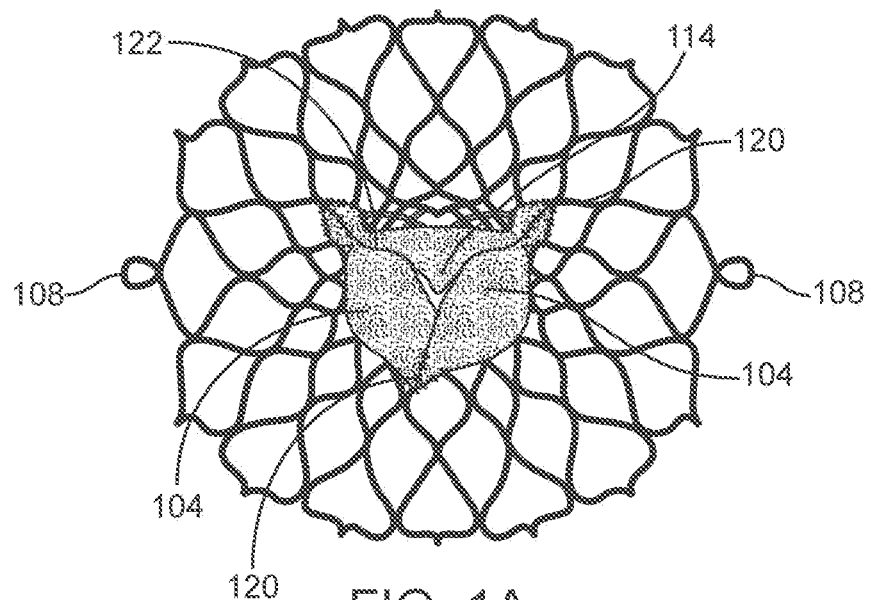
FIG. 1A is a top view illustration of the heart valve prosthesis of FIG. 1.
Figure 1B:
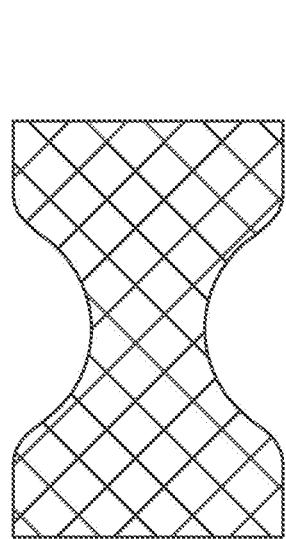
FIG. 1B is a side view illustration of an alternative configuration of a heart valve prosthesis for use in embodiments hereof.
Figure 1C:
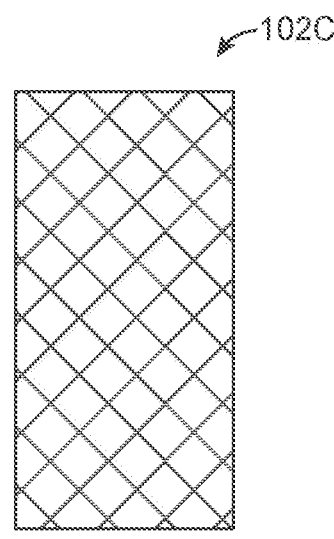
FIG. 1C is a side view illustration of an alternative configuration of a heart valve prosthesis for use in embodiments hereof.

In the embodiment depicted in FIGS. 1 and 1A, stent 102 of valve prosthesis 100 has a deployed asymmetric hourglass configuration including an enlarged first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102 may be designed with a number of different configurations and sizes to meet the different requirements of the location in which it may be implanted. When configured as a replacement for an aortic valve, second section 118 functions as an inflow end of heart valve prosthesis 100 and extends into and anchors within the aortic annulus of a patient's left ventricle, while first section 116 functions as an outflow end of heart valve prosthesis 100 and is positioned in the patient's ascending aorta. When configured as a replacement for a mitral valve, enlarged first section 116 functions as an inflow end of heart valve prosthesis 100 and is positioned in the patient's left atrium, while second section 118 functions as an outflow end of heart valve prosthesis 100 and extends into and anchors within the mitral annulus of a patient's left ventricle. For example, U.S. Patent Application Publication Nos. 2012/0101572 to Kovalsky et at, and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed asymmetric hourglass configuration of FIGS. 1 and 1A, the stent/valve support frame may have a symmetric hourglass configuration 102B shown in FIG. 1B, a generally tubular configuration 102C as shown in FIG. 1C, or other stent configuration or shape known in the art for valve replacement. Stent 102 also may include eyelets 108 that extend from first end 116 thereof for use in loading the heart valve prosthesis 100 into a delivery catheter (not shown).

As previously mentioned, heart valve prosthesis 100 includes a prosthetic valve component within the interior of stent 102. The prosthetic valve component is capable of blocking flow in one direction to regulate flow through heart valve prosthesis 100 via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration may alternatively be used in embodiments hereof. More particularly, if heart valve prosthesis 100 is configured for placement within a native valve having three leaflets such as the aortic, tricuspid, or pulmonary valves, heart valve prosthesis 100 may include three valve leaflets 104. If heart valve prosthesis 100 is configured for placement within a native valve having two leaflets such as the mitral valve, heart valve prosthesis 100 may include two valve leaflets 104. Valve leaflets 104 are sutured or otherwise securely and sealingly attached to the interior surface of stent 102 and/or graft material 106 which encloses or lines stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition Nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Delivery of heart valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve. Alternatively, heart valve prosthesis 100 may be balloon-expandable and delivery thereof may be accomplished via a balloon catheter as would be understood by one of ordinary skill in the art.

Figure 2:
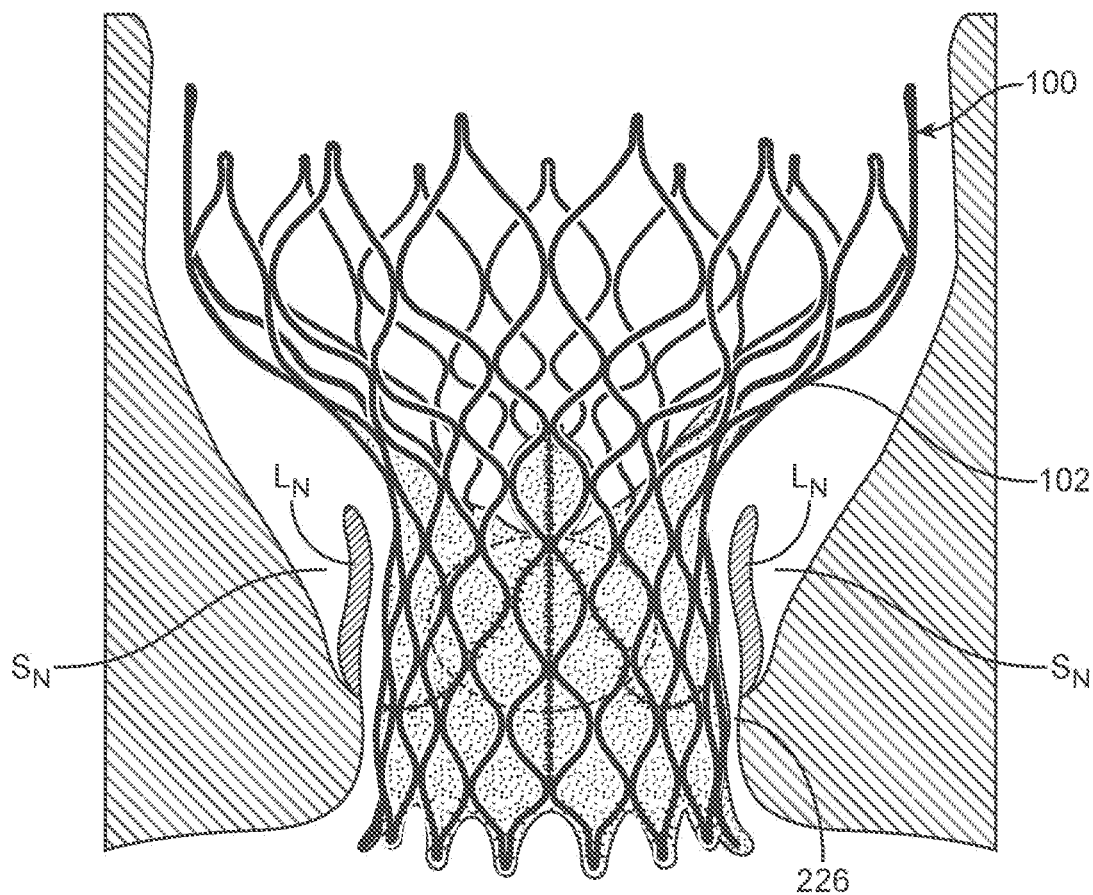
FIG. 2 is a side view illustration of the heart valve prosthesis of FIG. 1 implanted within a native valve annulus.

FIG. 2 is a side view illustration of heart valve prosthesis 100 implanted within a native heart valve, which is shown in section, having native leaflets $L_N$ and corresponding native sinuses $S_N$. When heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or cavities/crevices 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 3:
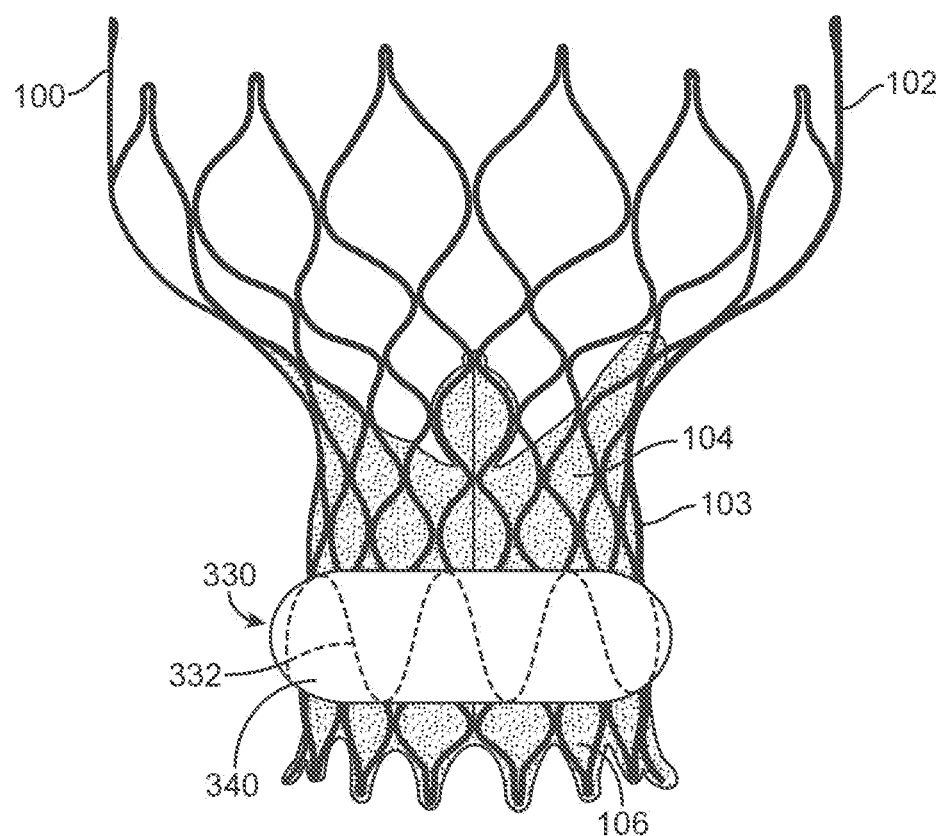
FIG. 3 is a side view of the heart valve prosthesis of FIG. 1 having an anti-paravalvular leakage component coupled thereto, wherein the anti-paravalvular leakage component includes a annular scaffold and an impermeable membrane that covers an outer surface of the annular scaffold.

Embodiments hereof relate to methods for delivering a heart valve prosthesis having a self-expanding anti-paravalvular leakage component thereon that functions to occlude or fill gaps between the perimeter of a heart valve prosthesis and the native valve annulus, thereby reducing, minimizing, or eliminating leaks there through. An anti-paravalvular leakage component 330 is shown in FIG. 3 in its deployed or expanded configuration, extending around an outer surface or perimeter 103 of heart valve prosthesis 100 to prevent paravalvular leakage in situ. Anti-paravalvular leakage component 330 extends in a radially outward direction relative to outer surface 103 of heart valve prosthesis 100, and exerts a radial pressure onto a native valve annulus when deployed in situ. More particularly, an expanded or deployed outer diameter of anti-paravalvular leakage component 330 is predetermined to be greater than the expanded outer diameter of stent 102. When deployed, anti-paravalvular leakage component 330 radially expands into and substantially fills any/all gaps or cavities/crevices between outer surface 103 of stent 102 and native valve tissue. "Substantially" as utilized herein means that blood flow through the target gap or cavity is occluded or blocked, or stated another way blood is not permitted to flow there through. Anti-paravalvular leakage component 330 blocks blood flow around the outer perimeter of prosthesis 100, thereby minimizing and/or eliminating any paravalvular leakage at the implantation site.

More particularly, anti-paravalvular leakage component 330 includes a radially-compressible ring or annular scaffold 332 (shown in phantom in FIG. 3) that is operable to self-expand and an impermeable or semi-impermeable membrane 340 that covers or extends over an outer surface of annular scaffold 332. Annular scaffold 332 is shown removed from anti-paravalvular leakage component 330 in FIG. 4. In addition, FIG. 5 shows annular scaffold 332 laid flat out for illustrative purposes, while FIG. 5A is a cross-sectional view taken along line A-A of FIG. 5. Annular scaffold 332 has sufficient radial spring force and flexibility to conformingly engage impermeable membrane 340 within a native heart valve annulus. Suitable materials for impermeable membrane 340 include but are not limited to impermeable or semi-impermeable materials such as a low-porosity woven fabric, such as polyester, Dacron fabric, or PTFE. Porous materials advantageously provide a medium for tissue ingrowth. Further, impermeable membrane 340 may be pericardial tissue or may be a knit or woven polyester, such as a polyester or PTFE knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side. Impermeable membrane 340 is coupled to annular scaffold 332 via sutures or other suitable mechanical connection.

Figure 4:
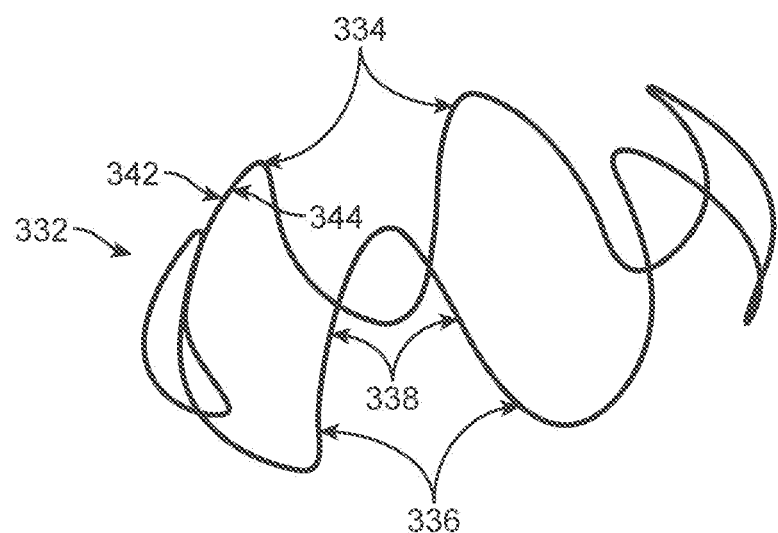
FIG. 4 is a perspective view of the annular scaffold of the anti-paravalvular leakage component of FIG. 3.
Figure 5:
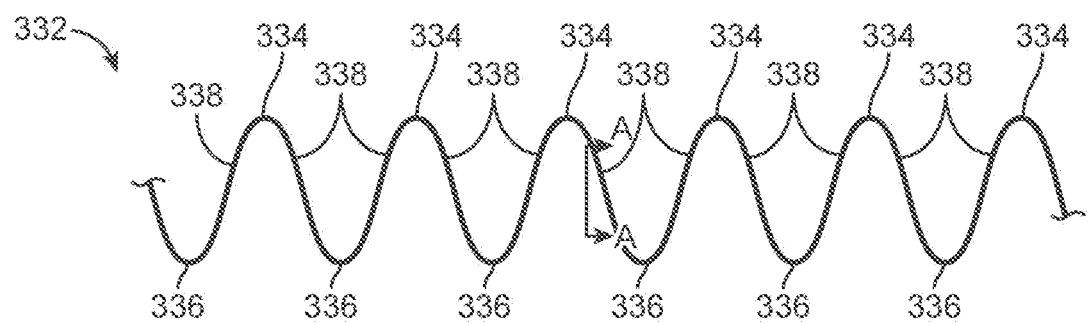
FIG. 5 illustrates the annular scaffold of the anti-paravalvular leakage component of FIG. 3 laid flat out for illustrative purposes.
Figure 5A:
FIG. 5A is a cross-sectional view taken along line A-A of FIG. 5.
Figure 7:
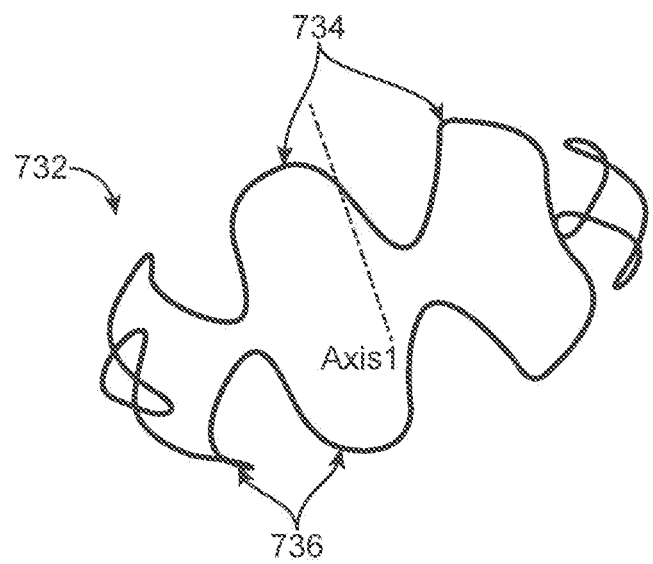
FIG. 7 is a perspective view of an annular scaffold for use in an anti-paravalvular leakage component, according to another embodiment hereof, wherein the annular scaffold includes an increased number of peaks and valleys relative to the annular scaffold of FIG. 4.

With reference to FIGS. 4 and 5, annular scaffold 332 is a sinusoidal patterned ring with a plurality of peaks 334, a plurality of valleys 336, and a plurality of segments 338 with peaks 334 and valleys 336 being formed between a pair of adjacent segments 338 as shown in FIG. 4. Peaks and valleys 334, 336 are bends or turns of the scaffold having opposing orientations. In the embodiment depicted in FIGS. 4 and 5, annular scaffold 332 includes six peaks 334 and six valleys 336. However, it would be obvious to one of ordinary skill in the art that the annular scaffold may include a higher or lower number of peaks and valleys. For example, FIG. 7 illustrates an embodiment in which an annular scaffold 732 includes eight peaks 734 and eight valleys 736. Conformability of the annular scaffold increases with a higher or increased number of peaks and valleys; however, the annular scaffold is more radially-compressible or collapsible for delivery with a lower or decreased number of peaks and valleys. In an embodiment, the annular scaffold includes between four and eighteen pairs of peaks and valleys.

In the embodiment depicted in FIG. 3, segments 338 bow or curve radially outward while both peaks 332 and valleys 334 bend or curve radially inward toward stent 102. Outer surface 342 of each segment 338 is convex, while an inner surface 344 of each segment 338 is concave. In one embodiment hereof, only peaks 332 are coupled to stent 102 while valleys 334 are unattached or free. In another embodiment hereof, only valleys 334 are coupled to stent 102 while peaks 332 are unattached or free. When only one end of annular scaffold 332 is constrained, i.e., either peaks 332 or valleys 334, the opposing unattached or free end of the annular scaffold is unconstrained, highly flexible, and has an ability to conform to an outer sheath utilized in deployment thereof. More particularly, the unattached peaks or valleys of the annular scaffold slide or ride along outer surface 103 of stent 102 when an outer sheath is advanced over the stent to compress/collapse heart valve prosthesis 100 for delivery. By sliding along outer surface 103 of stent 102, annular scaffold 332 and therefore anti-paravalvular leakage component 330 approaches a substantially linear delivery configuration within the outer sheath. When the outer sheath is retracted to deploy heart valve prosthesis 100, the unattached or free peaks or valleys of the annular scaffold return to their preset expanded or deployed shape because annular scaffold 332 is formed from a material having a mechanical memory. Mechanical memory may be imparted to annular scaffold 332 by thermal treatment to achieve a spring temper in stainless steel, for example, or to set a shape memory in a susceptible metal alloy, such as NiTi (Nitinol). In an alternate embodiment, a mechanical memory to return to the preset expanded or deployed shape may be imparted to a shape memory polymer that forms annular scaffold 332, such as any of the polymers disclosed in U.S. Pat. Appl. Pub. No. 2004/0111111 to Lin, which is herein incorporated by reference in its entirety.

In an embodiment, anti-paravalvular leakage component 330 is coupled to heart valve prosthesis 100 after manufacture of heart valve prosthesis 100. In another embodiment, anti-paravalvular leakage component 330 is manufactured in conjunction with, i.e., at the same time as, heart valve prosthesis 100. Regardless of whether anti-paravalvular leakage component 330 is formed concurrently with or subsequent to heart valve prosthesis 100, annular scaffold 332 of anti-paravalvular leakage component 330 may be formed from a single, continuous wire that may be solid or hollow and may have a different cross-section and/or size from stent 102 of heart valve prosthesis 100. More particularly, in an embodiment, stent 102 is formed via laser-cut manufacturing method and therefore a strut of the stent may have a non-circular cross-section, e.g., a square, rectangular, or polygonal cross-section, and a thickness ranging between 0.011-0.018 inches. Annular scaffold 332 may be formed from a single, continuous wire having a circular or round cross-section as shown in FIG. 5A with a diameter between 0.005-0.015 inches. In another embodiment, the cross-section of the wire that forms annular scaffold 332 may be an oval, elliptical, rectangular or ribbon-like, or any other suitable shape. By forming annular scaffold 332 of a relatively thinner or smaller wire as compared to a strut of stent 102, annular scaffold 332 has greater flexibility to conform to the inner surface of the native valve annulus including any surface irregularities that may be present, thereby filling any gaps or cavities/crevices that may be present between the heart valve prosthesis 100 and native tissue, while the thicker struts of stent 102 provide sufficient radial force to deploy the heart valve prosthesis into apposition with the native valve annulus. In another embodiment hereof, annular scaffold 332 of anti-paravalvular leakage component 330 may be integrally formed with stent 102 of heart valve prosthesis via a laser-cut manufacturing method. If integrally formed with stent 102, the cross-section of the wire/strut of annular scaffold 332 may be the same size and shape as a strut of the stent or may be of a different size and/or shape as the strut of the stent.

Figure 6:
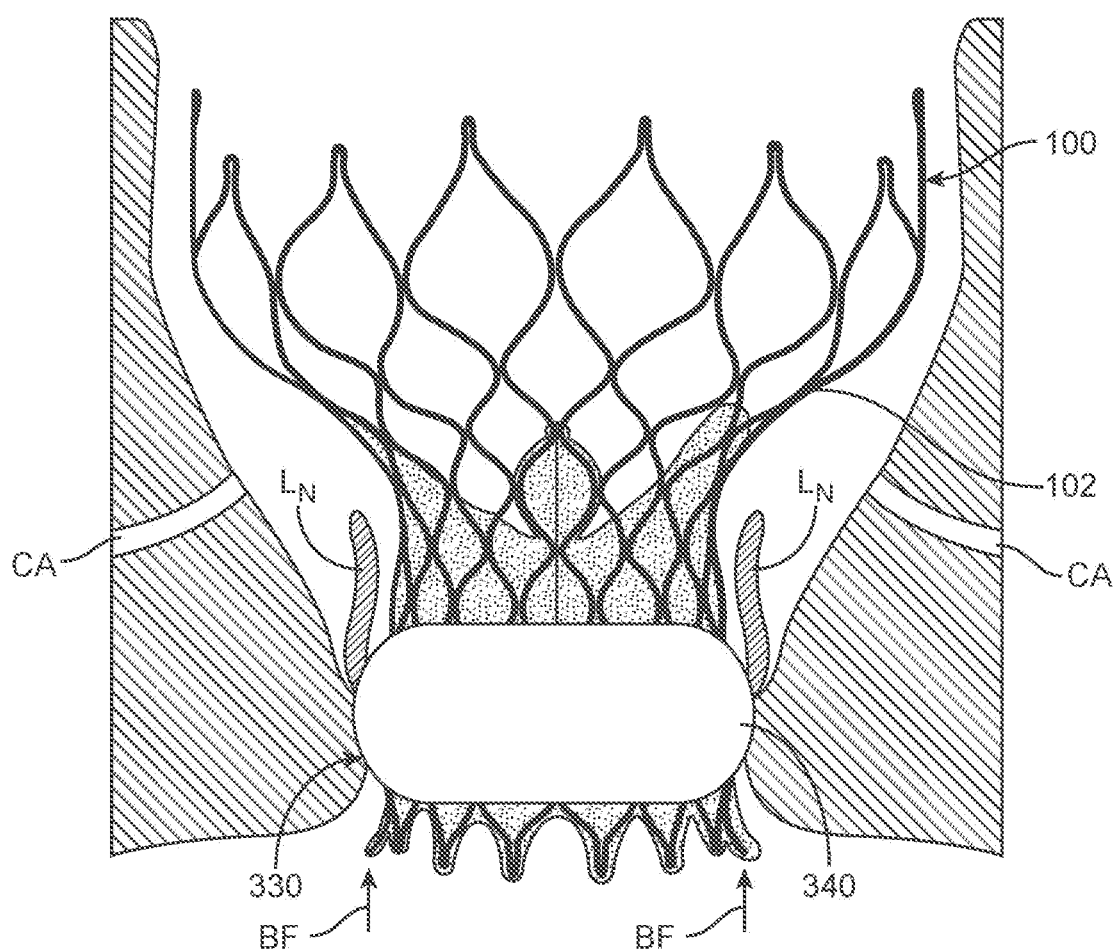
FIG. 6 is a side view illustration of the heart valve prosthesis of FIG. 3, having an anti-paravalvular leakage component coupled thereto, implanted within a native valve annulus.

Shown deployed within an aortic valve in FIG. 6, segments 338 of annular scaffold 332 protrude radially outward from heart valve prosthesis 100 to easily conform to calcified anatomy of the native valve while impermeable membrane 340 provides a mechanical barrier to the blood flowing through any gaps or cavities/crevices present between the heart valve prosthesis and the native valve tissue. Antegrade blood flow BF is illustrated by directional arrows in FIG. 6. Annular scaffold 332 is radially and circumferentially compliant due to its relatively small wire size, as described herein. With such maximized conformability, anti-paravalvular leakage component 330 functions as a continuous circumferential seal around the heart valve prosthesis to prevent or block blood flow between the outer surface or perimeter of the heart valve prosthesis and a native heart valve annulus.

In the embodiment of FIGS. 3-6, anti-paravalvular leakage component 330 is coupled to outer surface 103 of heart valve prosthesis 100 adjacent to second end 118 thereof. When deployed, anti-paravalvular leakage component 330 may be positioned in situ at the native valve annulus, slightly above the valve annulus, slightly below the valve annulus, or some combination thereof. Since the annular anti-paravalvular leakage component is coupled to outer surface 103 of heart valve prosthesis 100, longitudinal placement and/or the size and shape thereof is flexible and may be adjusted or adapted according to each application and to a patient's unique needs. For example, depending on the anatomy of the particular patient, the anti-paravalvular leakage component may be positioned on heart valve prosthesis 100 so that in situ the anti-paravalvular leakage component is positioned between heart valve prosthesis 100 and the interior surfaces of the native valve leaflets, between heart valve prosthesis 100 and the interior surfaces of the native valve annulus, and/or between heart valve prosthesis 100 and the interior surfaces of the left ventricular outflow track (LVOT).

Figure 8:
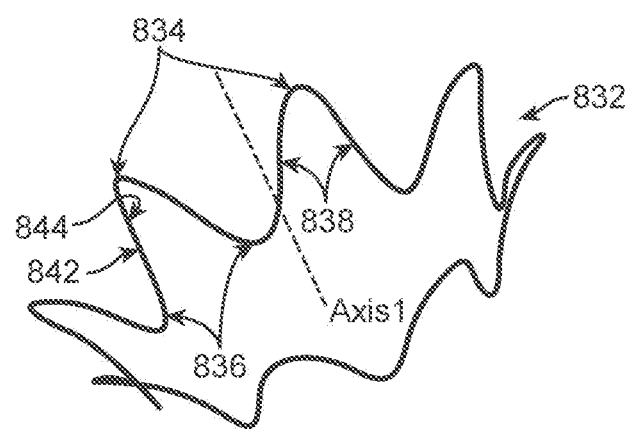
FIG. 8 is a perspective view of an annular scaffold for use in an anti-paravalvular leakage component, according to another embodiment hereof, wherein the annular scaffold includes peaks that curve or bow radially outward.

The shape or configuration of the annular scaffold may be optimized based on the design and application of the heart valve prosthesis. In another embodiment hereof depicted in FIGS. 8 and 9, an annular scaffold 832 includes segments 838 that curve or flare radially outward between valleys 836 that bend or curve radially inward for attachment to a stent of a heart valve prosthesis and peaks 834 that flare or curve radially outward. Outer surface 842 of each segment 838 is concave, while an inner surface 844 of each segment 838 is convex. Since only valleys 834 are coupled/constrained to the heart valve prosthesis and peaks 832 are unconstrained or free and highly flexible, annular scaffold 832 has an ability to conform to an outer sheath utilized in deployment thereof as described above.

Figure 9:
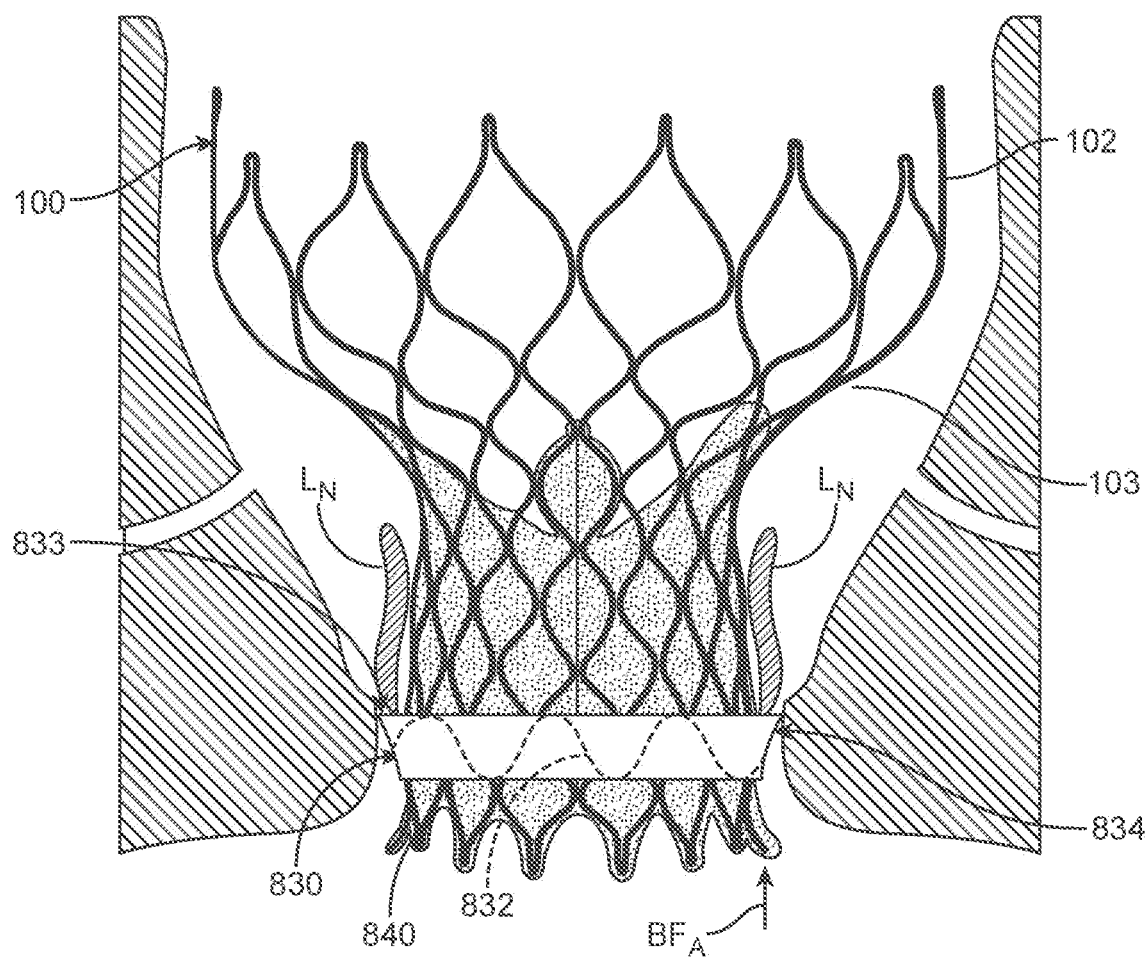
FIG. 9 is a side view illustration of an anti-paravalvular leakage component which used the annular scaffold of FIG. 8 implanted within a native valve annulus.

FIG. 9 illustrates an anti-paravalvular leakage component 830 coupled to heart valve prosthesis 100, which is deployed within an aortic valve having native valve leaflets $L_N$. Anti-paravalvular leakage component 830 includes an impermeable membrane 840 coupled to an outer surface of annular scaffold 832, thereby forming an open-ended pocket or compartment 833 around stent 102 between an inner surface of anti-paravalvular leakage component 830 and outer surface 103 of heart valve prosthesis 100. Open-ended pocket 833 catches and blocks any retrograde flow within the aortic valve, thereby preventing undesired regurgitation and preventing blood stagnation in and around the native valve sinuses. In addition, the configuration of anti-paravalvular leakage component 830, formed by flared, unconstrained peaks 834 and impermeable membrane 840 coupled to the outside surface of the annular scaffold, diverts or deflects antegrade blood flow away from heart valve prosthesis 100. Antegrade blood flow $BF_A$ is illustrated with a directional arrow in FIG. 9. By diverting or deflecting antegrade blood flow away from the heart valve prosthesis and catching retrograde blood flow with open-ended pocket 833, anti-paravalvular leakage component 830 formed with annular scaffold 832 functions as a continuous circumferential seal around the heart valve prosthesis to prevent or block blood flow between the outer surface or perimeter of the heart valve prosthesis and a native heart valve annulus.

Figure 10:
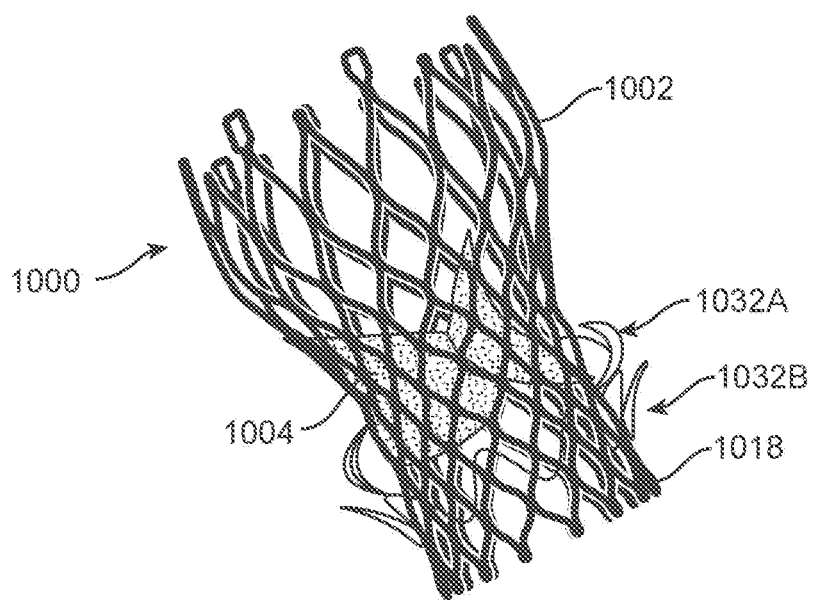
FIG. 10 is a perspective view of an annular scaffold for use in an anti-paravalvular leakage component, according to another embodiment hereof, wherein the annular scaffold includes a combination of peaks that curve radially inward and peaks that curve radially outward.

In yet another embodiment hereof, the anti-paravalvular leakage component may include two or more adjacent annular scaffolds. The adjacent annular scaffolds may have the same configuration, i.e., two adjacent annular scaffold 332 or two adjacent annular scaffold 832, or the adjacent annular scaffold may have different configurations. For example, FIG. 10 illustrates a heart valve prosthesis 1000 having a first annular scaffold 1032A and a second annular scaffold 1032B. Heart valve prosthesis 1000 includes a support frame or stent 1002 and a valve component 1004 secured therein, but graft material adjacent to a second end 1018 thereof is not shown for sake of clarity. Annular scaffold 1032A is similar to annular scaffold 332 and includes segments that bow or bulge radially outward while both peaks and valleys thereof bend or curve radially inward toward heart valve prosthesis 1000. Annular scaffold 1032B is similar to annular scaffold 832 and includes segments that are curved or flare radially outward between valleys that bend or curve radially inward for attachment to heart valve prosthesis 1000 and unconstrained peaks that flare or curve radially outward. Although not shown for sake of clarity, an impermeable membrane is coupled to each of annular scaffolds 1032A, 1032B to form two anti-paravalvular leakage components as described herein with respect to annular scaffolds 332, 832, respectively. In addition, although shown with annular scaffold 1032B adjacent to second end 1018 of heart valve prosthesis 1000, it will be apparent to one of ordinary skill in the art that annular scaffold 1032A may alternatively be located closer to second end 1018 than annular scaffold 1032B. The adjacent annular scaffolds may be positioned such their peaks and valleys are in phase with each other, or out of phase with each other for improved compressibility/collapsibility.

Figure 11:
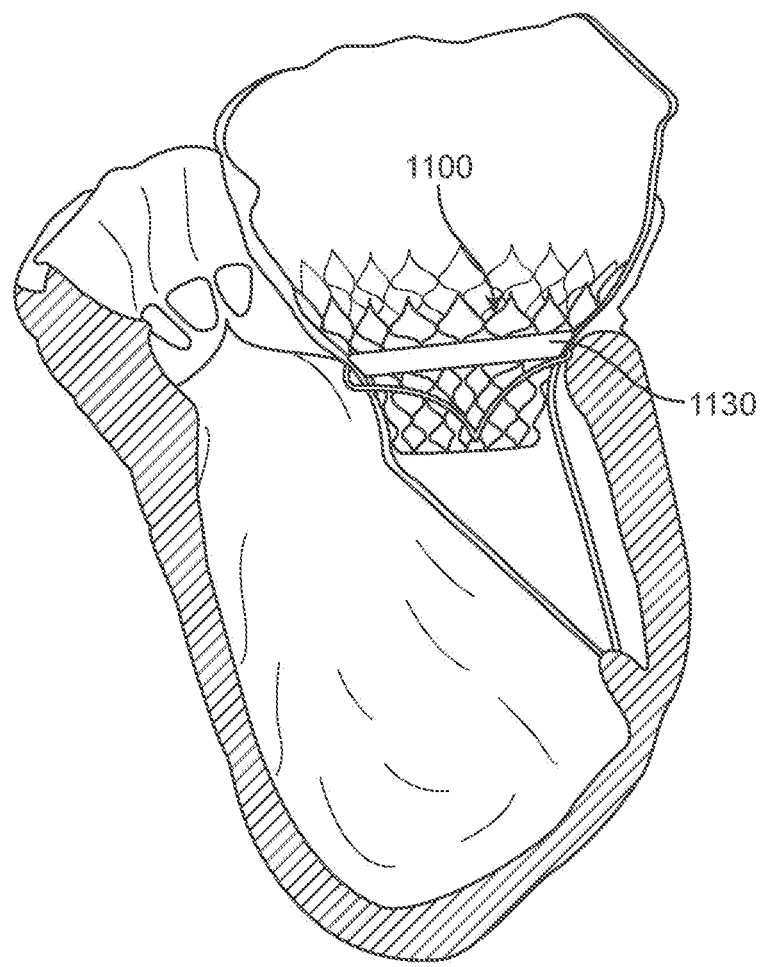
FIG. 11 is a side view illustration of a heart valve prosthesis, having an anti-paravalvular leakage component coupled thereto, implanted within a native mitral valve annulus.

Although embodiments depicted herein illustrate an anti-paravalvular leakage component integrated onto a heart valve prosthesis configured for implantation within an aortic valve, it would be obvious to one of ordinary skill in the art that an anti-paravalvular leakage component as described herein may be integrated onto a heart valve prosthesis configured for implantation implanted within other heart valves. For example, FIG. 11 illustrates an anti-paravalvular leakage component 1130 coupled to the outer surface or perimeter of a heart valve prosthesis 1100 implanted within a mitral valve.

Figure 12:
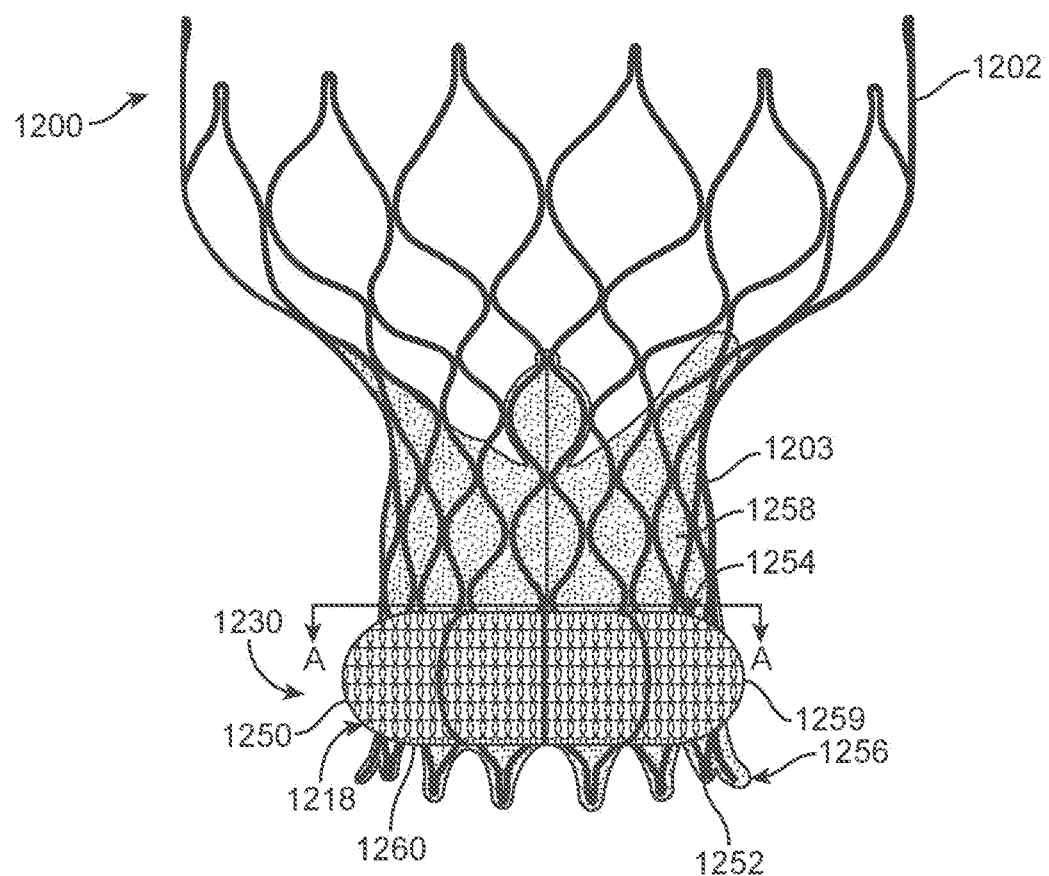
FIG. 12 is a side view of a heart valve prosthesis having an anti-paravalvular leakage component coupled thereto according to another embodiment hereof, wherein the anti-paravalvular leakage component includes a plurality of self-expanding segments and an annular sealing element coupled to an inside surface of the segments.

FIG. 12 illustrates an anti-paravalvular leakage component 1230, in its expanded or deployed configuration, coupled to a heart valve prosthesis 1200 according to another embodiment hereof. In this embodiment, anti-paravalvular leakage component 1230 includes a plurality of independent, self-expanding segments 1250 and an annular sealing element 1260. Annular sealing element 1260 is coupled to inner surfaces 1252 of segments 1250, and when the segments radially expand or deploy as described in more detail herein, annular sealing element 1260 is positioned between an outer surface 1203 of heart valve prosthesis 1200 and inner surfaces 1252 of the segments. As such, annular sealing element 1260 extends around the outer surface or perimeter of heart valve prosthesis 1200 and extends into and substantially fills any/all gaps or cavities/crevices between outer surface 1203 of heart valve prosthesis 1200 and native valve tissue to prevent paravalvular leakage in sin. In an embodiment hereof, annular sealing element 1260 may be formed from a swellable material that collapses easily and expands to a larger volume after implantation, such as but not limited to hydrogel or a collagen foam/sponge similar to the material commercially available under the trademark Angioseal. Other suitable material examples for annular sealing element 1260 include tissue, compressible foam materials, fabric, or compressible polymeric materials.

Figure 12A:
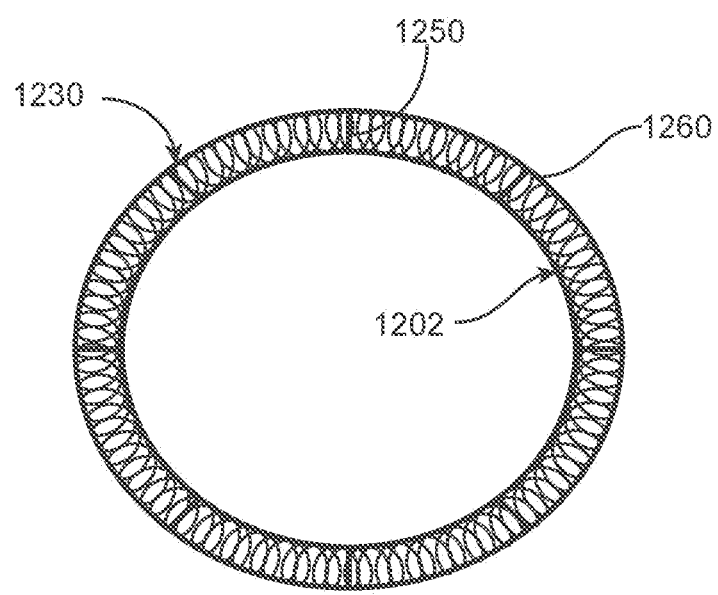
FIG. 12A is an end view of FIG. 12 taken along line A-A of FIG. 12.

Segments 1250 are coupled to an outer surface 1203 of heart valve prosthesis 1200. More particularly, first and second ends 1254, 1256 of segments 1250 are coupled to an outer surface 1203 of heart valve prosthesis 1200 via welding, sutures, or other suitable mechanical method. In another embodiment hereof, segments 1250 may be integrally formed with stent 1202 of heart valve prosthesis. Segments 1250 are spaced apart in approximately equal intervals or segments around heart valve prosthesis 1200 as shown in FIG. 12A, which is an end view taken along line A-A of FIG. 12. In another embodiment hereof, the segments may be spaced apart in non-equal intervals or segments around the outside of the heart valve prosthesis. For example, it may be desirable to position one or more segments at a location on the heart valve prosthesis corresponding to an area prone to leakage in situ, such as adjacent to the native valve commissures. Although shown with eight segments 1250, it will be understood by one of ordinary skill in the art that a greater or lesser number of segments may be utilized herein.

Figure 13A:
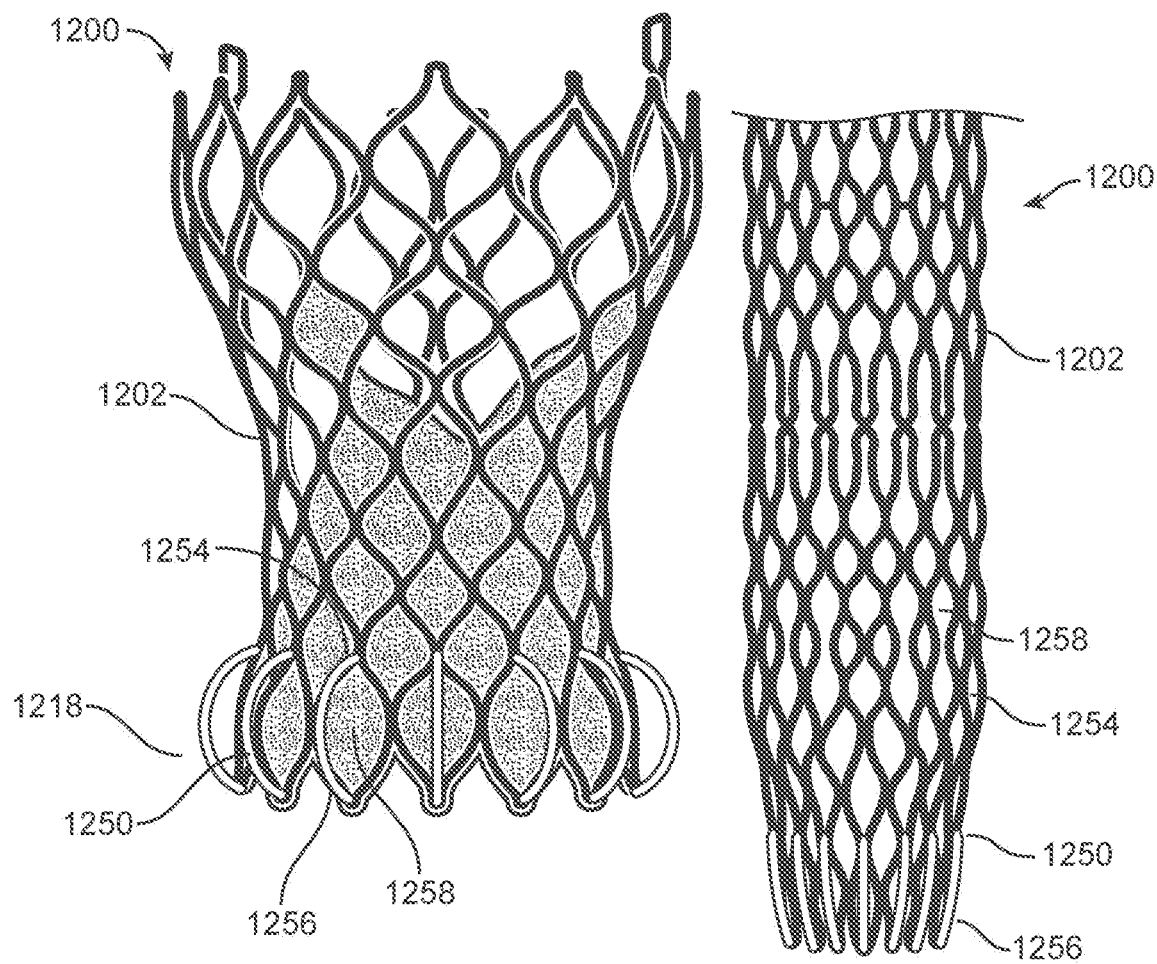
FIG. 13A illustrates the length of a diamond-shaped opening of a stent when the heart valve prosthesis of FIG. 13 is in a deployed or expanded configuration.
Figure 13A:
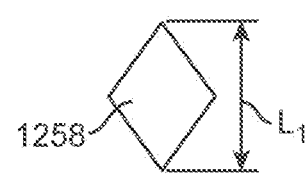
Figure 14A:
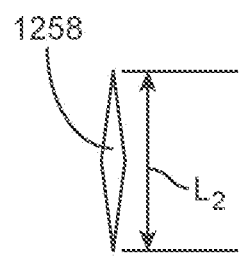
FIG. 14A illustrates the length of a diamond-shaped opening of a stent when the heart valve prosthesis of FIG. 13 is in a compressed or delivery configuration.

As best shown in FIG. 13, in which annular sealing element 1260 has been removed for clarity, ends 1254, 1256 of each segment 1250 are coupled to opposing peaks or apexes of a diamond-shaped opening 1258 of stent 1202 of heart valve prosthesis 1200. In this embodiment, segments 1250 are coupled to diamond-shaped openings adjacent to end 1218 of heart valve prosthesis 1200 but it will be understood that the segments may be coupled to diamond-shaped openings anywhere along the length of stent 1202. The longitudinal position of anti-paravalvular leakage component 1230 on heart valve prosthesis 1200 may vary depending upon application and configuration of the heart valve prosthesis. Coupling each segment 1250 to opposing peaks or apexes of a diamond-shaped opening 1258 of stent 1202 allows each segment to utilize the foreshortening of stent 1202 to its advantage because each segment 1250 aligns and packs/collapses within its corresponding opening 1258 when heart valve prosthesis 1200 is crimped for delivery. More particularly, as shown in FIG. 14, when heart valve prosthesis 1200 is crimped onto a catheter (not shown) for delivery thereof, openings 1258 are longitudinally stretched and elongate to a length $L_2$, which is shown in FIG. 14A. An arc length of each segment 1250 is approximately equal to length L2, the crimped length of opening 1258 such that each segment 1250 is stretched flat or flush over its corresponding opening 1258 when crimped. Stated another way, each segment 1250 is straightened when heart valve prosthesis 1200 is crimped for delivery and the straightened segment 1250 is in line or flush with the crimped stent 1202. When each segment 1250 is stretched flat or flush over its corresponding opening 1258, the material of annular seating element 1260 is compressed and pulled inside stent 1202 via openings 1258. Accordingly, the addition of anti-paravalvular leakage component 1230 advantageously does not increase, or minimally increases, the packing profile of heart valve prosthesis 1200 so that heart valve prosthesis 1200 has the ability to pack in lower profile delivery systems.

When heart valve prosthesis 1200 is deployed, as shown in FIG. 13, stent 1202 foreshortens and the length of openings 1258 return to their deployed length $L_1$, which is shown in FIG. 13A. Segment 1250, and annular sealing member 1260 attached thereto, self-expand radially outward as shown in FIG. 12 and FIG. 13. An outer surface 1259 of each segment is convex, while the inner surface 1252 of each segment is concave. Similar to segments 338 of annular scaffold 332 described with respect to FIG. 6 herein, segments 1250 bow or curve radially outward to easily conform to calcified anatomy of the native valve while annular sealing member 1260 provides a mechanical barrier to the blood flowing through any gaps or cavities/crevices present between the heart valve prosthesis and the native valve tissue. In this embodiment, since annular sealing member 1260 is positioned between segments 1250 and prosthesis 1200, the sealing member is protected from being unintentionally moved or shifted during delivery.

Similar to previous embodiments described herein, anti-paravalvular leakage component 1230 may be formed concurrently with or subsequent to heart valve prosthesis 1200 and each segment 1250 of anti-paravalvular leakage component 1230 may be formed from a wire that may be solid or hollow and may have a different cross-section and/or size from stent 1202 of heart valve prosthesis 1200. For example, segments 1250 may be formed of a relatively thinner or smaller wire as compared to a strut of stent 1202 such that anti-paravalvular leakage component 1230 has greater flexibility to conform to the inner surface of the native valve annulus including any surface irregularities that may be present, thereby filling any gaps or cavities/crevices that may be present between the heart valve prosthesis 1200 and native tissue, while the thicker struts of stent 1202 provide sufficient radial force to deploy the heart valve prosthesis into apposition with the native valve annulus.

Segments 1250 are radially-compressible and self-expanding. In order to self-expand, segments 1250 may be made from a metallic material having a mechanical memory to return to the preset expanded or deployed shape. Mechanical memory may be imparted to segments 1250 by thermal treatment to achieve a spring temper in stainless steel, for example, or to set a shape memory in a susceptible metal alloy, such as NiTi (Nitinol) or Co—Cr (Cobalt-Chrome). In an alternate embodiment, a mechanical memory to return to the preset expanded or deployed shape may be imparted to a shape memory polymer that forms segments 1250, such as any of the polymers disclosed in U.S. Pat. Appl. Pub. No. 2004/0111111 to Lin, which is herein incorporated by reference in its entirety.

Figure 15:
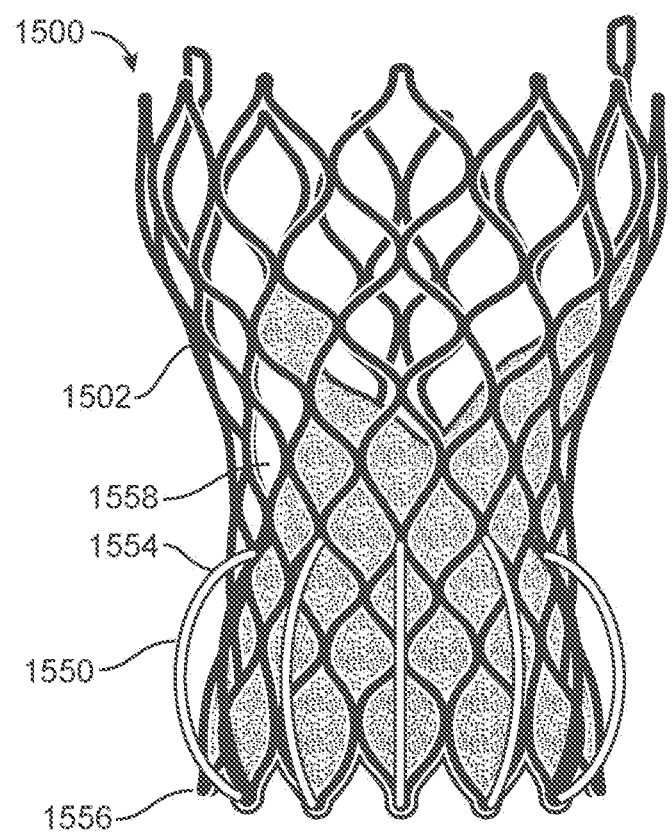
FIG. 15 is a side view of a heart valve prosthesis having an anti-paravalvular leakage component coupled thereto according to another embodiment hereof, wherein the anti-paravalvular leakage component includes a plurality of self-expanding segments that extend over two longitudinally adjacent diamond-shaped openings of a stent.
Figure 15A:
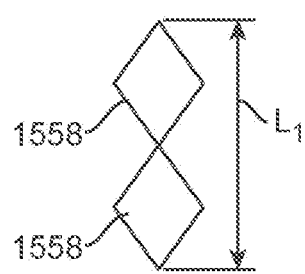
FIG. 15A illustrates the length of a diamond-shaped opening of a stent when the heart valve prosthesis of FIG. 15 is in a deployed or expanded configuration.
Figure 15B:
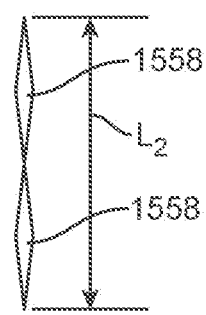
FIG. 15B illustrates the length of a diamond-shaped opening of a stent when the heart valve prosthesis of FIG. 15 is in a compressed or delivery configuration.

It will be understood by one of ordinary skill in the art that the length of anti-paravalvular leakage component 1230 is not limited to the embodiment shown in FIG. 12. For example, as shown in the embodiment of FIG. 15, in which the annular sealing element has been removed for clarity, each segment 1250 may extend over two openings 1558 of a stent 1502 of a heart valve prosthesis 1500. Ends 1554, 1556 of each segment 1550 are coupled to opposing peaks or apexes of two longitudinally-adjacent diamond-shaped opening 1558. As explained above, each segment 1550 aligns and packs/collapses within its corresponding openings 1558 when heart valve prosthesis 1500 is crimped for delivery. An arc length of each segment 1550 is approximately equal to length $L_2$, the crimped length of two longitudinally-adjacent diamond-shaped openings 1558, as shown in FIG. 15B. When heart valve prosthesis 1500 is deployed, as shown in FIG. 15, stent 1502 foreshortens and the length of two longitudinally-adjacent diamond-shaped openings 1558 return to their deployed length $L_1$, which is shown in FIG. 15A. Segment 1550, and the annular sealing member attached thereto, self-expand or bow radially outward to conform to the anatomy of the native valve.

Figure 16:
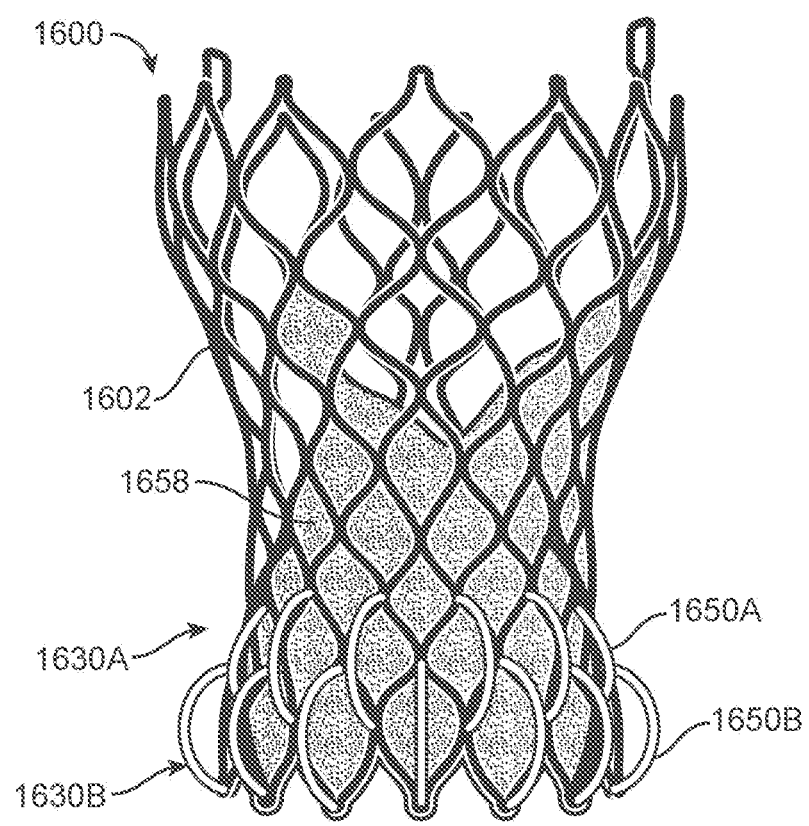
FIG. 16 is a side view of a heart valve prosthesis having two anti-paravalvular leakage components coupled thereto according to another embodiment hereof.

In addition, two or more anti-paravalvular leakage components may be included on a heart valve prosthesis. For example, FIG. 16 illustrates a heart valve prosthesis 1600 having a first anti-paravalvular leakage component 1630A and a second anti-paravalvular leakage component 1630B. Although not shown for sake of clarity, an annular sealing element is coupled inside surfaces of segments 1650A, 1650B to form two anti-paravalvular leakage components 1630A, 1630B, respectively, as described herein with respect to anti-paravalvular leakage component 1230. Segments 1650A, 1650B are shown coupled to adjacent rows of openings 1658 of stent 1602 such that anti-paravalvular leakage components 1630A, 1630B are abutting against each other, but anti-paravalvular leakage components 1630A, 1630B may alternatively be positioned at longitudinally spaced apart locations on heart valve prosthesis 1600.

In the embodiments of FIGS. 12-16, segments of the anti-paravalvular leakage components in the expanded configuration are orthogonal to the outer surface of the tubular stent. "Orthogonal" to the outer surface of the tubular stent as used herein means that a plane defined by each expanded segment is perpendicular with respect to a tangential plane of the tubular stent taken through the first and second attachments points. When positioned in situ, deformation of the valve prosthesis by the surrounding native anatomy as an orthogonal force may require straightening of the orthogonal segment and distortion of the tubular stent to which the segment is attached. However, in another embodiment hereof, when the anti-paravalvular leakage component is in the expanded configuration the segments may be oblique to the outer surface of the tubular stent. "Oblique" to the outer surface of the tubular stent as used herein means that a plane defined by each segment is non-perpendicular with respect to a tangential plane of the tubular stent taken through the first and second attachments points. The plane defined by each segment may form an angle between 20 and 80 degrees with respect to a tangential plane of the outer surface of the tubular stent. When positioned in sin, deformation of the valve prosthesis by the surrounding native anatomy as a non-orthogonal force results in bending or pivoting of the oblique segments at the first and second attachments points, thereby increasing conformability of the anti-paravalvular leakage component with respect to the surrounding native anatomy. Further, since oblique segments bend or pivot rather than fatten to accommodate the surrounding native anatomy, such bending does not distort the tubular stent and the oblique segments may be designed independently of the tubular frame to optimize force and movement thereof for sealing purposes.

Figure 17:
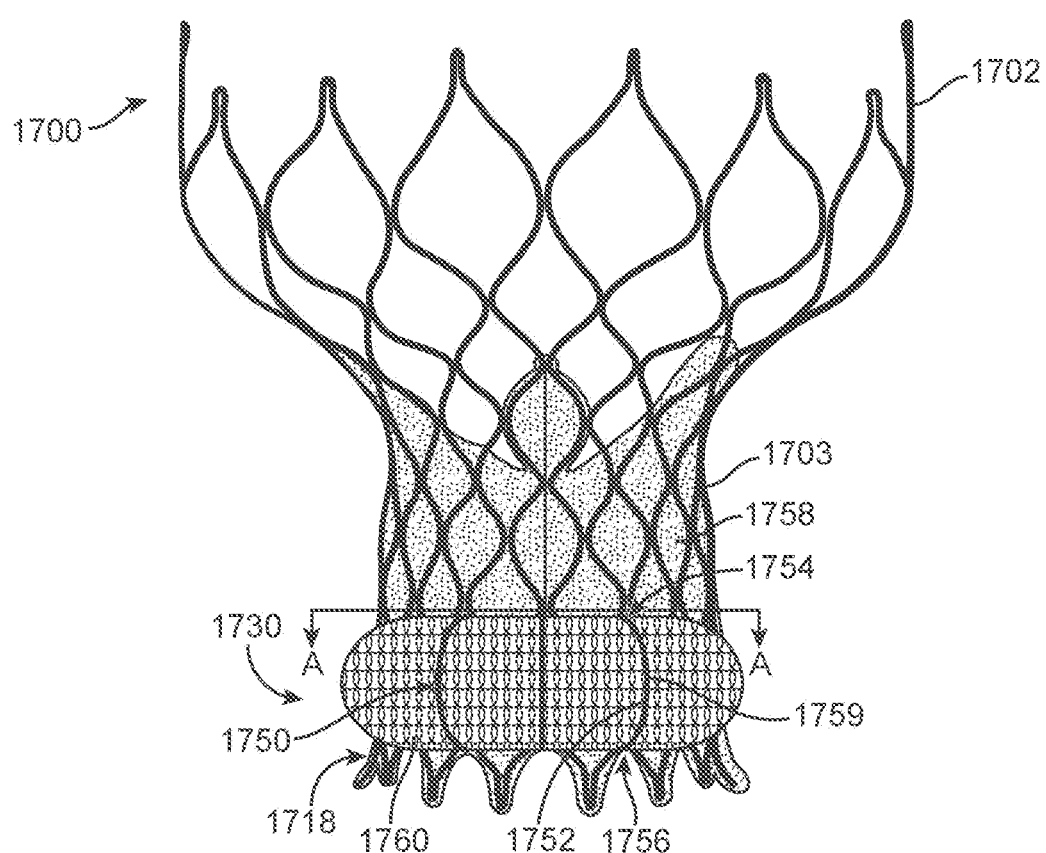
FIG. 17 is a side view of a heart valve prosthesis having an anti-paravalvular leakage component coupled thereto according to another embodiment hereof, wherein the anti-paravalvular leakage component includes a plurality of oblique self-expanding segments and an annular sealing element coupled to an inside surface of the segments.
Figure 17A:
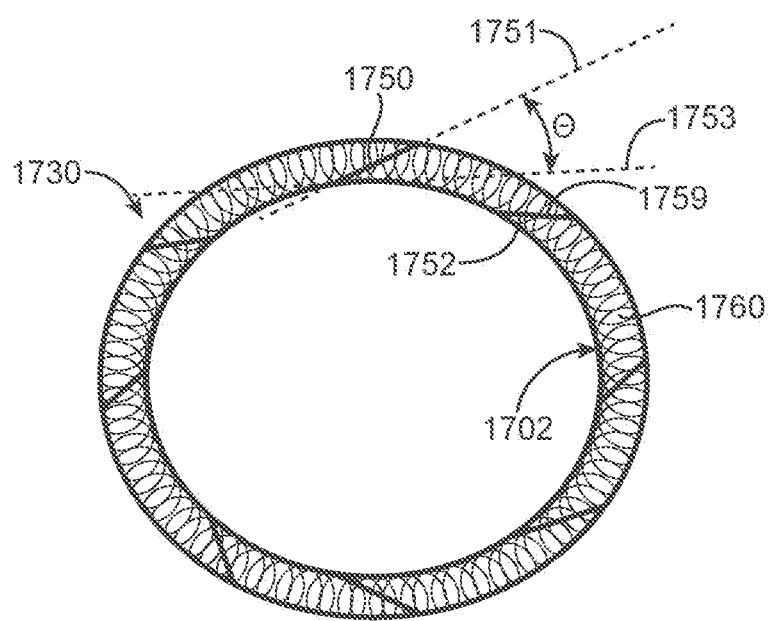
FIG. 17A is an end view of FIG. 17 taken along line A-A of FIG. 17.

More particularly, FIGS. 17 and 17A illustrate an embodiment hereof in which an anti-paravalvular leakage component 1730, in its expanded or deployed configuration, includes a plurality of independent, self-expanding segments 1750 that are oblique to an outer surface 1703 of a tubular stent 1702 of a heart valve prosthesis 1700. Similar to anti-paravalvular leakage component 1230, anti-paravalvular leakage component 1730 includes segments 1750 and an annular sealing element 1760. Segments 1750 are coupled to outer surface 1703 of heart valve prosthesis 1700, and an outer surface 1759 of each segment is convex while the inner surface 1752 of each segment is concave. More particularly, first and second ends 1754, 1756 of segments 1750 are coupled to an outer surface 1703 of heart valve prosthesis 1700 via welding, sutures, or other suitable mechanical method. In another embodiment hereof, segments 1750 may be integrally formed with stent 1702 of heart valve prosthesis. In this embodiment, ends 1754, 1756 of each segment 1750 are coupled to opposing peaks or apexes of a diamond-shaped opening 1758 of stent 1702 of heart valve prosthesis 1700. Since ends 1754, 1756 of each segment 1750 are coupled to opposing peaks or apexes of a diamond-shaped opening 1758, ends 1754, 1756 are coupled to stent 1702 at axially spaced apart locations but are not circumferentially spaced apart. In further embodiments that will be described in more detail below, the ends of each segment may be coupled to the stent at axially spaced apart and circumferentially spaced apart locations. Further, in this embodiment, segments 1750 are coupled to diamond-shaped openings adjacent to end 1718 of heart valve prosthesis 1700 but it will be understood that the segments may be coupled to diamond-shaped openings anywhere along the length of stent 1702. The longitudinal position of anti-paravalvular leakage component 1730 on heart valve prosthesis 1700 may vary depending upon application and configuration of the heart valve prosthesis.

As best shown in FIG. 17A, segments 1750 in the expanded or deployed configuration are oblique to outer surface 1703 of tubular stent 1702. More particularly, each segment 1750 in the expanded or deployed configuration defines a first plane 1751. A second or tangential plane 1753 of stent 1702 is taken through the first and second attachments points of ends 1754, 1756 of each segment 1750. First plane 1751 as defined by expanded segment 1750 forms an angle Θ with second or tangential plane 1753 of stent 1702 and is non-perpendicular with respect to second or tangential plane 1753 of stent 1702. In an embodiment hereof, angle Θ may range between 1 and 89 degrees. In an embodiment hereof, angle Θ may range between 20 and 80 degrees. As angle Θ increases, the radial height or distance of segment 1750 with respect to the outer surface 1703 of tubular stent 1702 increases. More particularly, the angle, height, length, and/or geometry of segment 1750 are all parameters that may be modified to optimize the stress and/or bending movement experienced by segment 1750, as well as the force exerted by segment 1750, when segment 1750 is positioned in situ to accommodate the surrounding native anatomy for sealing purposes. Stated another way, the angle, height, length, and/or geometry of segment 1750 are parameters that may be modified in order for segment 1750 to achieve optimal sealing performance in situ.

Segments 1750 are spaced apart in approximately equal intervals or segments around heart valve prosthesis 1700 as shown in FIG. 17A, which is an end view taken along line A-A of FIG. 17. In another embodiment hereof, the segments may be spaced apart in non-equal intervals or segments around the outside of the heart valve prosthesis. For example, as will be explained in more detail herein, it may be desirable to position one or more segments at a location on the heart valve prosthesis corresponding to an area prone to leakage in situ, such as adjacent to the native valve commissures. Although shown with eight segments 1750, it will be understood by one of ordinary skill in the an that a greater or lesser number of segments may be utilized herein. Conformability of the anti-paravalvular leakage component increases with a higher or increased number of segments; however, the anti-paravalvular leakage component is more radially-compressible or collapsible for delivery with a lower or decreased number of segments.

As shown in FIG. 17A, annular sealing element 1760 is coupled to inner surfaces 1752 of segments 1750, and when the segments radially expand or deploy, annular sealing element 1760 is positioned between outer surface 1703 of heart valve prosthesis 1700 and inner surfaces 1752 of the segments. As such, annular sealing element 176 circumferentially surrounds or extends around the outer surface or perimeter of heart valve prosthesis 1700 and extends into and substantially fills any/all gaps or cavities/crevices between outer surface 1703 of heart valve prosthesis 1700 and native valve tissue to prevent paravalvular leakage in situ. Since annular sealing member 1760 is positioned between segments 1750 and prosthesis 1700, the sealing member is protected from being unintentionally moved or shifted during delivery. In an embodiment hereof, annular sealing element 1760 may be formed from a swellable material that collapses easily and expands to a larger volume after implantation, such as but not limited to hydrogel or a collagen foam/sponge similar to the material commercially available under the trademark Angioseal. Other suitable material examples for annular sealing element 1760 include tissue, compressible foam materials, fabric, or compressible polymeric materials.

Figure 17B:
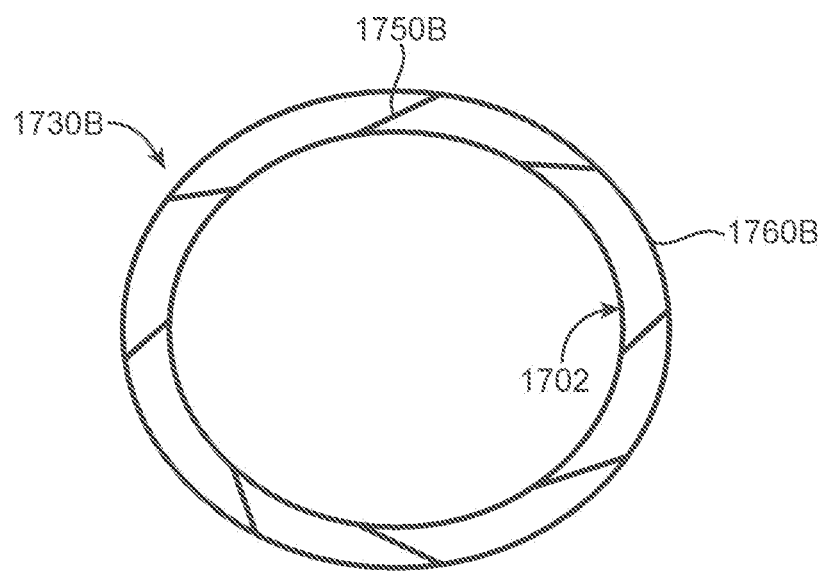
FIG. 17B is an end view of FIG. 17 taken along line A-A of FIG. 17 according to an alternative embodiment hereof in which the annular sealing element is coupled to an outer surface of the segments.

In another embodiment hereof shown in FIG. 17B, anti-paravalvular leakage component 1730B includes annular sealing element 1760B and oblique segments 1750B. Annular sealing element 1760B is coupled to outer surfaces of segments 1750B to form an impermeable or semi-permeable membrane that covers or extends over segments 1750B. Segments 1750B protrude radially outward from the tubular stent to easily conform to calcified anatomy of the native valve while annular sealing element 1760B provides a mechanical barrier to the blood flowing through any gaps or cavities/crevices present between the heart valve prosthesis and the native valve tissue. Since annular sealing member 1760B is positioned over segments 1750B, the sealing member advantageously does not increase, or minimally increases, the packing profile of the heart valve prosthesis so that the heart valve prosthesis has the ability to pack in lower profile delivery systems. Suitable materials for annular sealing element 1760B include but are not limited to impermeable or semi-permeable materials such as a low-porosity woven fabric, such as polyester, Dacron fabric, or PTFE. Porous materials advantageously provide a medium for tissue ingrowth. Further, annular sealing element 1760B may be pericardial tissue or may be a knit or woven polyester, such as a polyester or PTFE knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side. Annular sealing element 1760B is coupled to segments 1750B via sutures or other suitable mechanical connection.

Figure 17C:
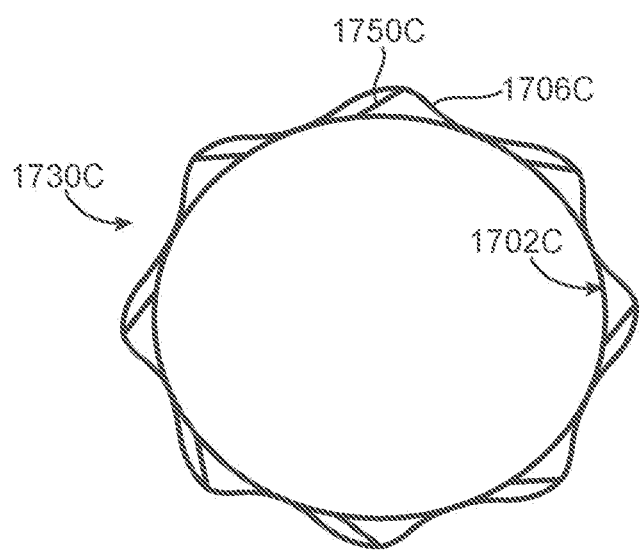
FIG. 17C is an end view of FIG. 17 taken along line A-A of FIG. 17 according to an alternative embodiment hereof in which the annular sealing element is formed via the graft material of the heart valve prosthesis.

In another embodiment hereof, the graft material of the heart valve prosthesis may form the annular sealing element of the anti-paravalvular leakage component. More particularly, as shown in the embodiment of FIG. 17C, anti-paravalvular leakage component 1730C includes oblique segments 1750C which are coupled or attached to graft material 1706C which encloses or lines stent 1702C of the heart valve prosthesis. For example, segments 1750C may be stitched to graft material 1706C. In one embodiment, graft material 1706C may be selected so as to have the ability to stretch during deployment of the heart valve prosthesis. In another embodiment, the heart valve prosthesis may be configured with extra or additional graft material 1706C, e.g., folds, which may be pulled out during deployment of the heart valve prosthesis. When deployed, graft material 1706C which is coupled to segments 1750C is pulled radially away from the outer surface of stent 1702C such that the graft material forms an impermeable or semi-permeable membrane that provides a mechanical barrier to the blood flowing through any gaps or cavities/crevices present between the heart valve prosthesis and the native valve tissue. When graft material 1706C lines stent 1702C, and thus is coupled to an inside surface thereof, graft material 1706C may be pulled through the diamond-shaped openings or cells formed within stent 1702C. Since the graft material of the heart valve prosthesis forms the annular sealing member, this embodiment advantageously does not increase the packing profile of the heart valve prosthesis so that the heart valve prosthesis has the ability to pack in lower profile delivery systems.

Figure 18:
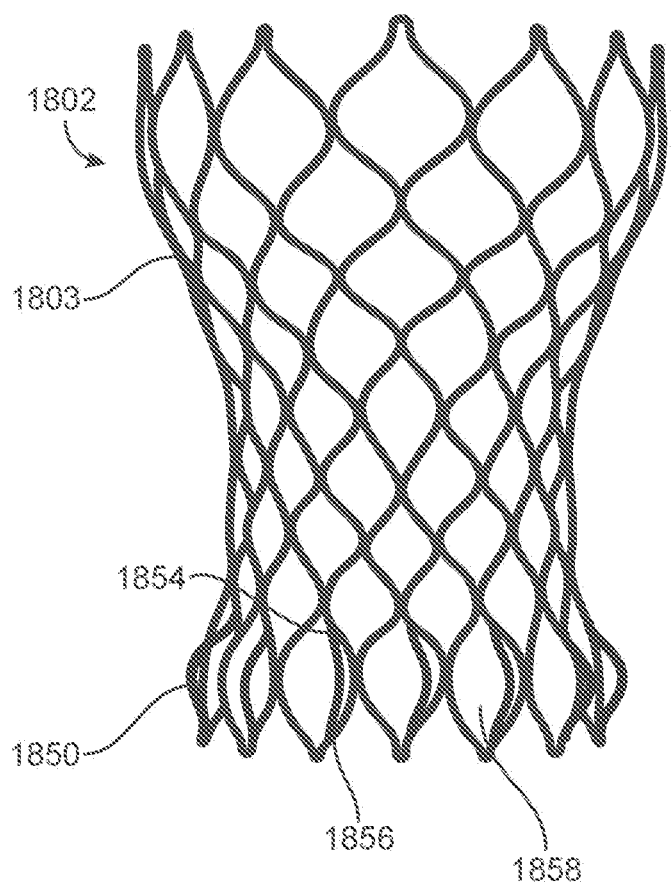
FIG. 18 is a side view of the heart valve prosthesis having an anti-paravalvular leakage component coupled thereto according to another embodiment hereof, wherein the anti-paravalvular leakage component includes a plurality of oblique self-expanding segments and the annular sealing element has been removed for clarity.
Figures 19A, 19B:
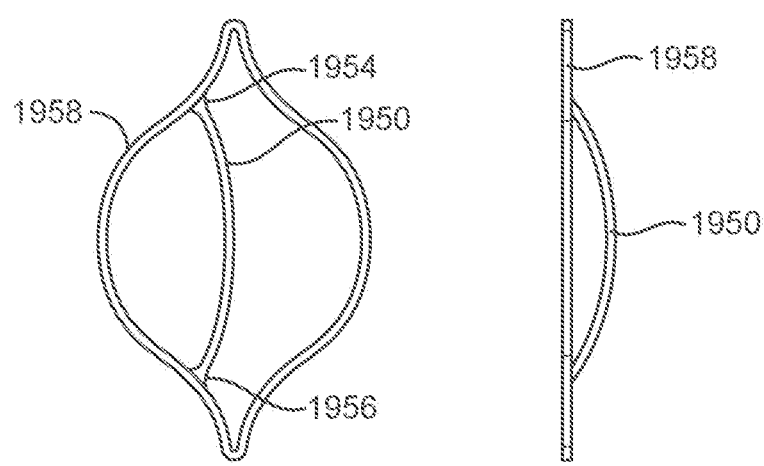
FIGS. 19A-19B illustrate front and side views, respectively, of one or more diamond-shaped openings of a stent, wherein an oblique self-expanding segment according to another embodiment hereof is coupled to the stent.

The oblique self-expanding segments of FIG. 17 may have other configurations, and the size, shape, or configuration of the annular scaffold may be optimized based on the design and application of the heart valve prosthesis. FIGS. 18-30B illustrate various exemplary configurations for oblique self-expanding segments utilized in embodiments hereof. For example, FIG. 18 depicts a plurality of independent, self-expanding segments 1850 that are oblique to an outer surface 1803 of a tubular stent 1802. In FIG. 18, the annular sealing component of the anti-paravalvular leakage component has been removed for clarity. Similar to previous embodiments, first and second ends 1854, 1856 of segments 1850 are coupled to or formed integrally with an outer surface 1803 of tubular stent 1802. In this embodiment, however, ends 1854, 1856 of each segment 1850 are not coupled to opposing peaks or apexes of a diamond-shaped opening 1858 of stent 1802 but rather are coupled to adjacent or consecutive sides of the diamond-shaped opening 1858. Accordingly, the length or size of segments 1850 are shorter or less than the length or size of segments 1750. Ends 1854, 1856 are coupled to stent 1802 at axially-spaced apart locations but are not circumferentially spaced apart. In this embodiment, segments 1850 are coupled to adjacent sides of the right half or portion of diamond-shaped opening 1858, but it will be understood that the segments may be coupled to the opposing or left half of the diamond-shaped opening as shown in FIGS. 19A-19B. FIGS. 19A-19B, which are front and side views of an isolated diamond-shaped opening 1958 of a stent, illustrate another embodiment hereof in which an oblique self-expanding segment 1950 is coupled to adjacent or consecutive sides on the left half or portion of the diamond-shaped opening 1958. Ends 1954, 1956 of segment 1950 are coupled to diamond-shaped opening 1958 at axially-spaced apart locations but are not circumferentially spaced apart. Segment 1950 is shown in its expanded or deployed configuration.

Figures 20A, 20B:
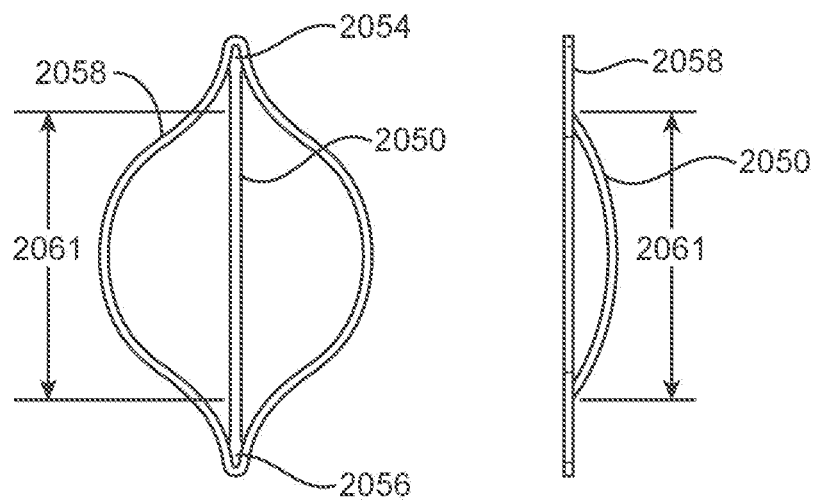
FIGS. 20A-20B illustrate front and side views, respectively, of one or more diamond-shaped openings of a stent, wherein an oblique self-expanding segment according to another embodiment hereof is coupled to the stent.

FIGS. 20A-20B, which are front and side views of an isolated diamond-shaped opening 2058 of a stent, illustrate another embodiment hereof in which an oblique self-expanding segment 2050 is coupled to opposing peaks or apexes of a diamond-shaped opening 2058. In this embodiment, however, only a middle portion 2061 of segment 2050 bends or curves radially away from the outer surface of the tubular stent rather than the full or entire length of the segment. Accordingly, the length or size of the radially-extending portions, i.e., middle portions 2061, of segments 2050 is shorter or less than the full length or size of segments 2050. Ends 2054, 2056 of segment 2050 are coupled to diamond-shaped opening 2058 at axially-spaced apart locations but are not circumferentially spaced apart. Segment 2050 is shown in its expanded or deployed configuration.

Figures 21A, 21B:
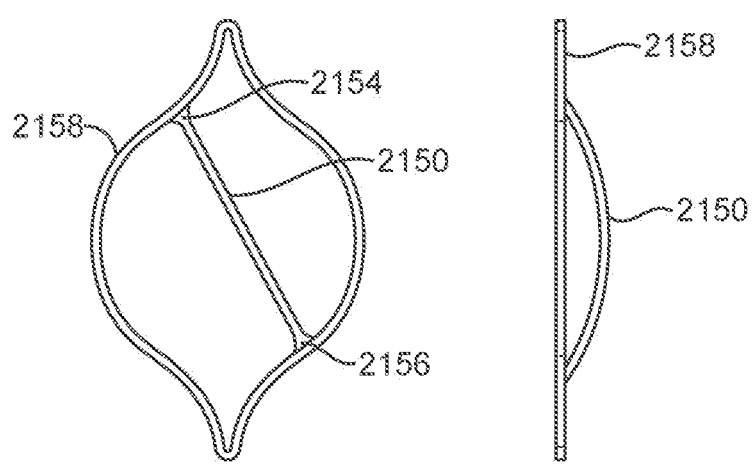
FIGS. 21A-21B illustrate front and side views, respectively, of one or more diamond-shaped openings of a stent, wherein an oblique self-expanding segment according to another embodiment hereof is coupled to the stent.

FIGS. 21A-21B, which are front and side views of an isolated diamond-shaped opening 2158 of a stent, illustrate another embodiment hereof in which an oblique self-expanding segment 2150 is coupled to diagonally-opposing sides of a diamond-shaped opening 2158. Ends 2154, 2156 of segment 2150 are coupled to diamond-shaped opening 2158 at axially spaced apart locations and circumferentially spaced apart locations. Segment 2150 is shown in its expanded or deployed configuration.

FIGS. 22A-22B, which are front and side views of an isolated diamond-shaped opening 2258 of a stent, illustrate another embodiment hereof in which an oblique self-expanding segment 2250 is coupled to adjacent or consecutive sides of a diamond-shaped opening 2158. In this embodiment, however, a middle portion 2261 of segment 2250 has a different curvature than the remaining length of the segment. Stated another way, middle portion 2261 of segment 2250 includes an additional bump or bulge along the length of segment 2250. Ends 2154, 2256 of segment 2250 are coupled to diamond-shaped opening 2258 at axially-spaced apart locations but are not circumferentially spaced apart. Segment 2250 is shown in its expanded or deployed configuration.

FIGS. 23A-23B, which are front and side views of an isolated diamond-shaped opening 2358 of a stent, illustrate another embodiment hereof in which an oblique self-expanding segment 2350 is coupled to diagonally-opposing sides of a diamond-shaped opening 2358, in this embodiment, segment 2350 has a sinusoidal or wavy configuration along the length thereof. Ends 2354, 2356 of segment 2350 are coupled to diamond-shaped opening 2358 at axially spaced apart locations and circumferentially spaced apart locations. Segment 2350 is shown in its expanded or deployed configuration.

FIGS. 24A-24B, which are front and side views of an isolated diamond-shaped opening 2458 of a stent, illustrate another embodiment hereof in which an oblique self-expanding segment 2450 is U-shaped and coupled to opposing sides of a diamond-shaped opening 2458. Ends 2454, 2456 of segment 2450 are coupled to diamond-shaped opening 2458 at circumferentially spaced apart locations but not axially spaced apart locations. Segment 2450 is shown in its expanded or deployed configuration. U-shaped as used herein includes segments having two opposing side portions 2463A, 2463B with ends that converge together from a bottom or apex curved portion 2465. As will be understood by those of ordinary skill in the art, "side" and "bottom" are relative terms and utilized herein for illustration purposes only. The two opposing side portions 2463A, 2463B of the U-shaped segment 2450 may be slanted or angled relative to each other, as shown in FIG. 24A, or may extend parallel to each other. Further, the U-shaped segment 2450 may be considerably longer, shorter, wider, or narrower than shown. In this embodiment, as best shown in the side view of FIG. 24B, U-shaped segment 2450 flares radially outward such that bottom or apex curved portion 2465 is most radially spaced away from the stent. An outer surface 2459 of U-shaped segment 2450 is concave, while an inner surface 2452 of U-shaped segment 2450 is convex. However, the U-shaped segment may have other expanded or deployed configurations such as the one shown in FIGS. 25A-25B. FIGS. 25A-25B, which are front and side views of an isolated diamond-shaped opening 2558 of a stent, illustrate another embodiment hereof in which an oblique self-expanding segment 2550 is U-shaped and coupled to opposing sides of a diamond-shaped opening 2558. Ends 2554, 2556 of segment 2550 are coupled to diamond-shaped opening 2558 at circumferentially spaced apart locations but not axially spaced apart locations. Segment 2550 is shown in its expanded or deployed configuration. In this embodiment, U-shaped segment 2550 curves radially outward such that at least portions of opposing side portions 2563A, 2563B as well as bottom curved portion 2565 are most radially spaced away from the stent. An outer surface 2559 of U-shaped segment 2550 is convex, while an inner surface 2552 of U-shaped segment 2550 is concave.

Figures 26A, 26B:
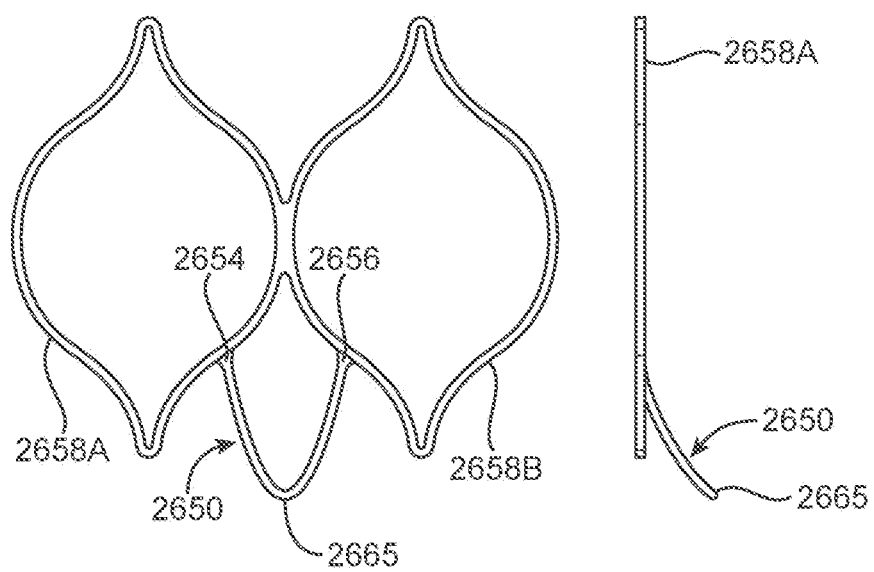
FIGS. 26A-26B illustrate front and side views, respectively, of one or more diamond-shaped openings of a stent, wherein an oblique self-expanding segment according to another embodiment hereof is coupled to the stent.
Figures 27A, 27B:
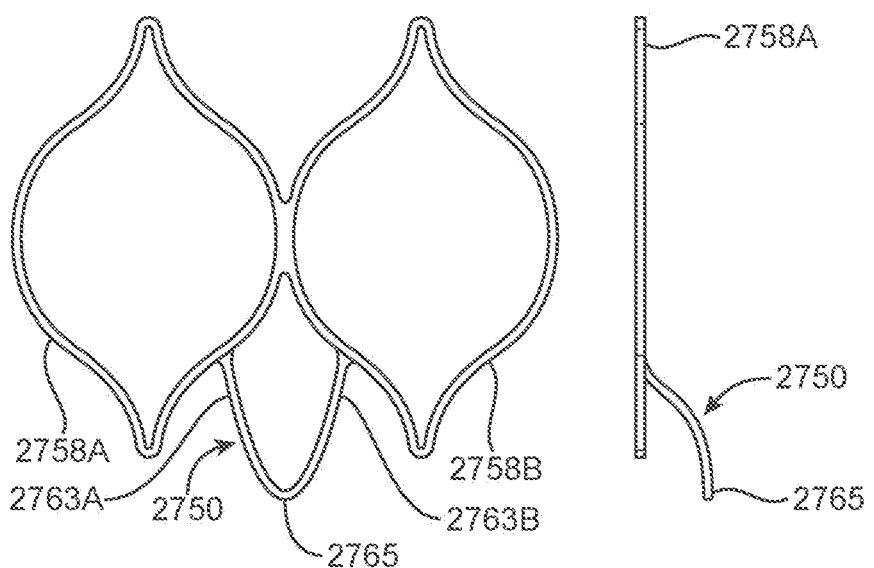
FIGS. 27A-27B illustrate front and side views, respectively, of one or more diamond-shaped openings of a stent, wherein an oblique self-expanding segment according to another embodiment hereof is coupled to the stent.

FIGS. 26A-26B, which are front and side views of two isolated diamond-shaped openings 2658A, 2658B of a stent, illustrate another embodiment hereof in which an oblique self-expanding segment 2650 is U-shaped and coupled to adjacent sides of diamond-shaped openings 2658A, 2658B. Ends 2654, 2656 of segment 2650 are coupled to and span across diamond-shaped openings 2658A, 2658B at circumferentially spaced apart locations but not axially spaced apart locations. Segment 2650 is shown in its expanded or deployed configuration. In this embodiment, as best shown in the side view of FIG. 26B, U-shaped segment 2650 flares radially outward such that bottom or apex curved portion 2665 is most radially spaced away from the stent similar to U-shaped segment 2450 described above. However, the U-shaped segment may have other expanded or deployed configurations such as the one shown in FIGS. 27A-27B. FIGS. 27A-27B, which are front and side views of two isolated diamond-shaped openings 2758A, 2758B illustrate another embodiment hereof in which an oblique self-expanding segment 2750 is U-shaped and U-shaped segment 2750 curves radially outward such that at least portions of opposing side portions 2763A, 2763B as well as bottom curved portion 2765 are most radially spaced away from the stent similar to U-shaped segment 2550 described above.

Figures 28A, 28B:
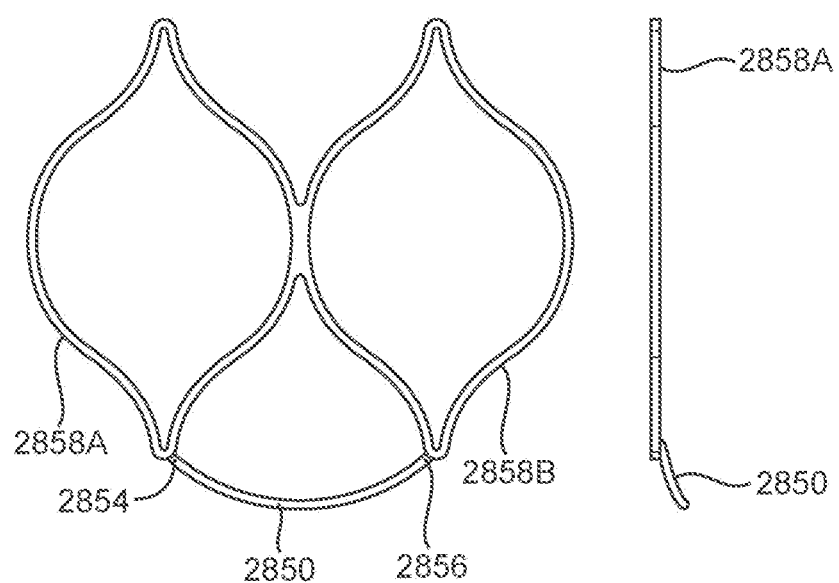
FIGS. 28A-28B illustrate front and side views, respectively, of one or more diamond-shaped openings of a stent, wherein an oblique self-expanding segment according to another embodiment hereof is coupled to the stent.

FIGS. 28A-28B, which are front and side views of two isolated diamond-shaped openings 2858A, 2858B of a stent, illustrate another embodiment hereof in which an oblique self-expanding segment 2650 is coupled to adjacent peaks or apexes of diamond-shaped openings 2858A, 2858B. Ends 2854, 2856 of segment 2850 are coupled to and span across diamond-shaped openings 2858A, 2858B at circumferentially spaced apart locations but not axially spaced apart locations. Segment 2850 is shown in its expanded or deployed configuration.

Figures 29A, 29B:
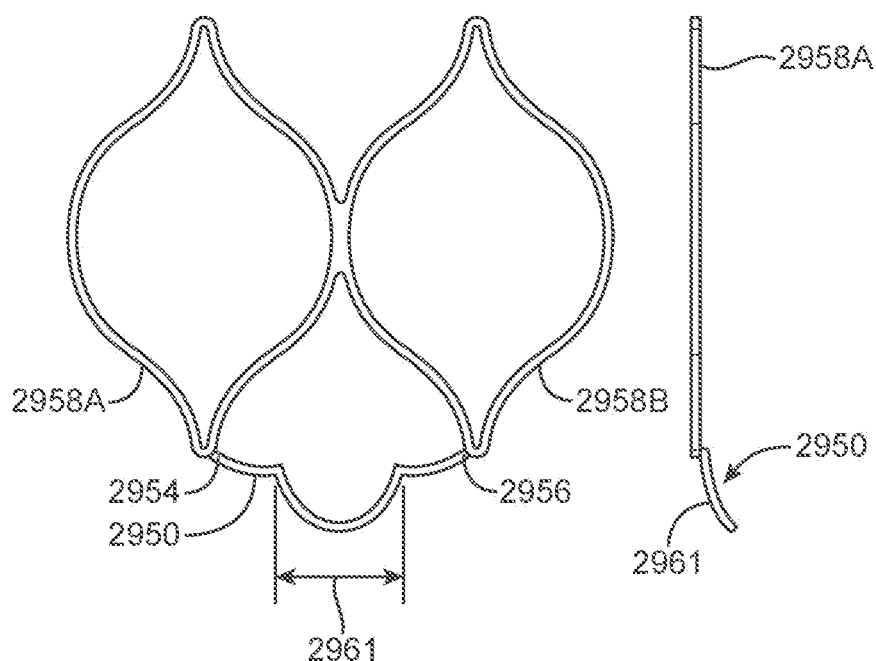
FIGS. 29A-29B illustrate front and side views, respectively, of one or more diamond-shaped openings of a stent, wherein an oblique self-expanding segment according to another embodiment hereof is coupled to the stent.
Figures 30A, 30B:
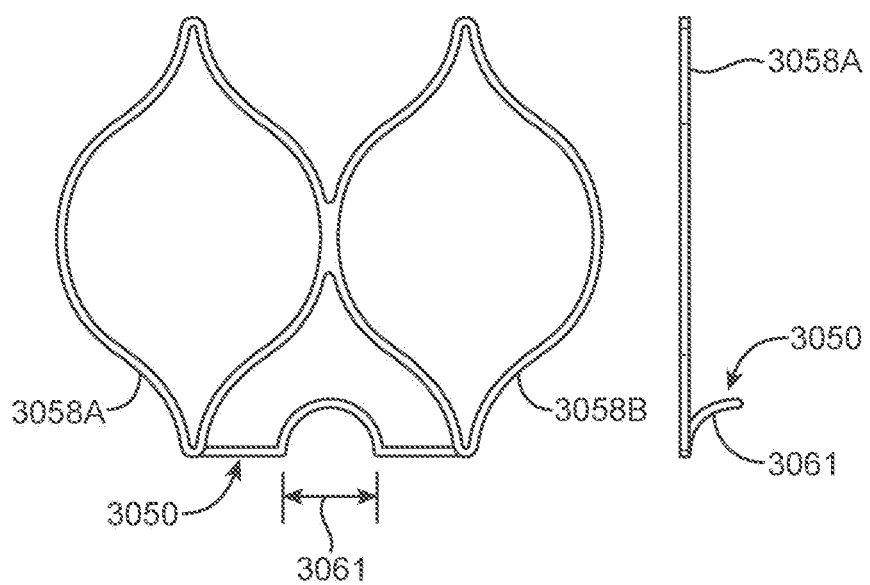
FIGS. 30A-30B illustrate front and side views, respectively, of one or more diamond-shaped openings of a stent, wherein an oblique self-expanding segment according to another embodiment hereof is coupled to the stent.

FIGS. 29A-29B, which are front and side views of two isolated diamond-shaped openings 2958A, 2958B of a stent, illustrate another embodiment hereof in which an oblique self-expanding segment 2950 is coupled to adjacent peaks or apexes of diamond-shaped openings 2958A, 2958B. In this embodiment, however, only a middle portion 2961 of segment 2950 extends radially away from the outer surface of the tubular stent rather than the full or entire length of the segment. Ends 2954, 2956 of segment 2950 are coupled to and span across diamond-shaped openings 2958A, 2958B at circumferentially spaced apart locations but not axially spaced apart locations. Segment 2950 is shown in its expanded or deployed configuration. Middle portion 2961 may be oriented to extend or curve away from diamond-shaped openings 2958A, 2958B as shown in FIG. 29A. In another embodiment hereof, shown in FIGS. 30A-30B, a middle portion 3061 of an oblique self-expanding segment 3050 may be oriented to extend or curve towards diamond-shaped openings 3058A, 3058B.

Figure 31:
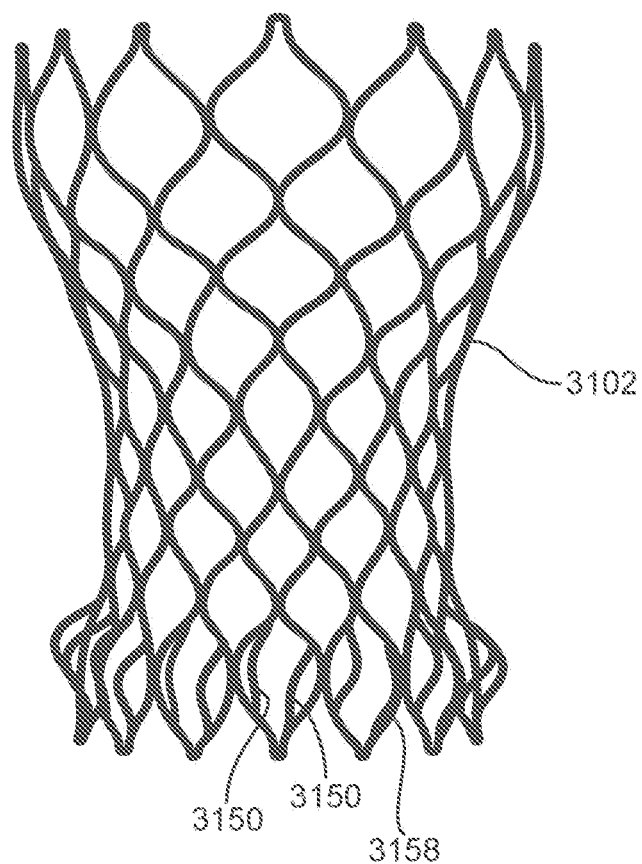
FIG. 31 is an enlarged side view of a portion of a stent, wherein each diamond-shaped opening of the stent includes two oblique self-expanding segments according to an embodiment hereof.
Figures 32A, 32B:
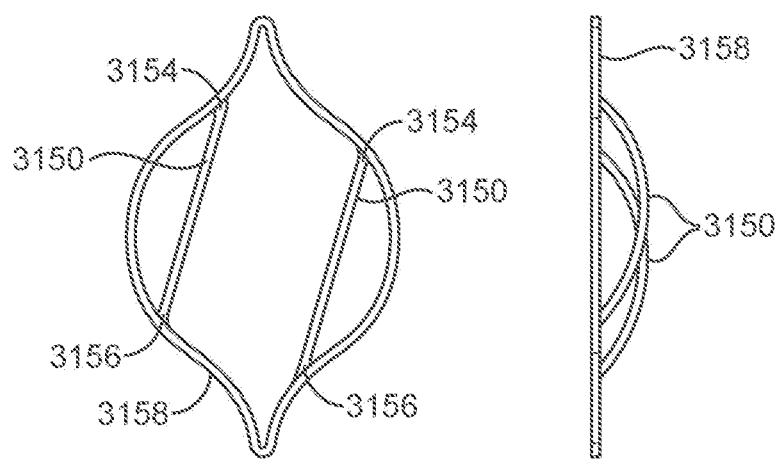
FIGS. 32A-32B are front and side views, respectively, of a diamond-shaped opening of the stent of FIG. 31.

FIGS. 31, 32A, and 32B illustrate another embodiment hereof in which two oblique self-expanding segments 3150 are coupled to a single diamond-shaped opening 3158 of a stent 3102. FIG. 31 is an enlarged view of a portion of stent 3102, with each diamond-shaped opening 3158 including two oblique self-expanding segments 3150. In FIG. 31, the annular sealing component of the anti-paravalvular leakage component has been removed for clarity. FIGS. 32A-32B are front and side views of an isolated diamond-shaped opening 3158 of stent 3102. Ends 3154, 3156 of each segment 3150 are coupled to adjacent or consecutive sides of diamond-shaped opening 3158 at axially spaced apart locations and circumferentially spaced apart locations. Segments 3150 are shown in their expanded or deployed configuration. Providing two oblique segments that extend over one diamond-shaped opening of the tubular stent provides additional structure or support for the anti-paravalvular leakage component, and conformability of the anti-paravalvular leakage component increases due to the higher or increased number of segments. The anti-paravalvular leakage component may include two segments extending over each diamond-shaped opening around the circumference of the tubular stent as shown in FIG. 31, or may include two segments extending over select diamond-shaped openings around the circumference of the tubular stent. For example, it may be desirable to position two segments extending over select diamond-shaped openings at a location on the heart valve prosthesis corresponding to an area prone to leakage in situ, such as adjacent to the native valve commissures.

Figure 33:
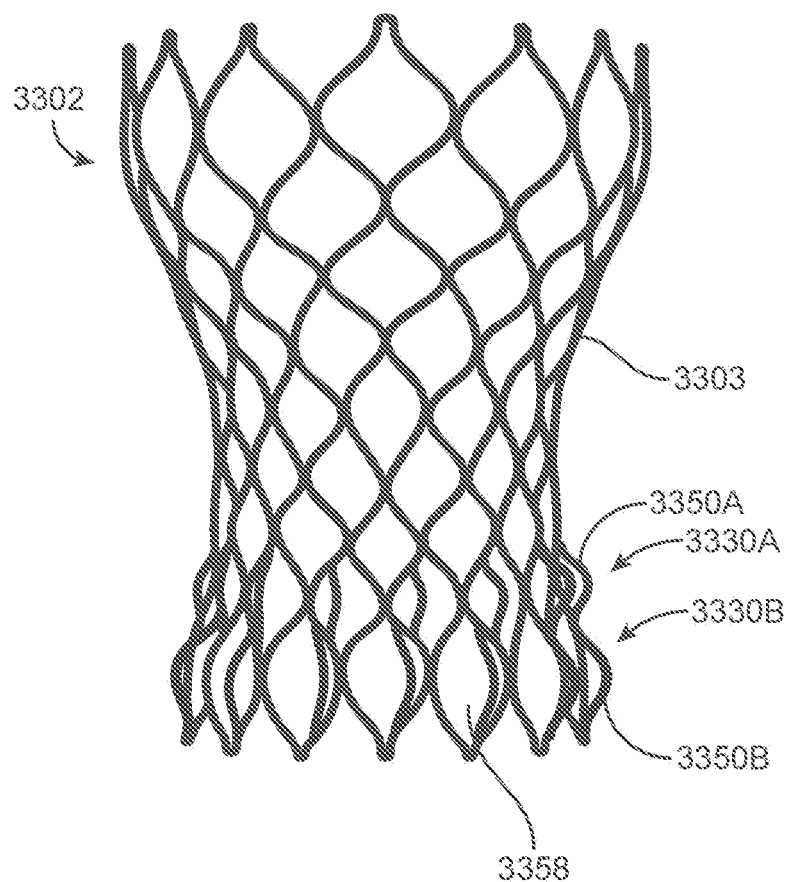
FIG. 33 is a side view of a heart valve prosthesis having two anti-paravalvular leakage components coupled thereto according to another embodiment hereof, wherein the anti-paravalvular leakage components each include a plurality of oblique self-expanding segments and the annular sealing elements have been removed for clarity.

In addition, similar to described above with respect to FIG. 16, two or more anti-paravalvular leakage components may be included on a heart valve prosthesis, FIG. 33 illustrates a stent 3302 for a heart valve prosthesis, the stent including a first anti-paravalvular leakage component 3330A and a second anti-paravalvular leakage component 3330B. Although not shown for sake of clarity, an annular sealing element is coupled to segments 3350A, 3350B to form two anti-paravalvular leakage components 3330A, 3330B, respectively. Segments 3350A, 3350B are oblique to an outer surface 3303 of tubular stent 3302, and are shown coupled to adjacent rows of diamond-shaped openings 3358 of stent 3302 such that anti-paravalvular leakage components 3330A, 3330B are abutting against each other. In another embodiment hereof (now shown), anti-paravalvular leakage components 3330A, 3330B may alternatively be positioned at longitudinally spaced apart locations on tubular stent 3302.

In embodiments hereof, it may be desirable for the flexibility or conformability of the anti-paravalvular leakage component at the plurality of segments to vary around the circumference of the tubular stent when the anti-paravalvular leakage component is in the expanded configuration. For example, it may be desirable to have one or more segments with increased flexibility or conformability (and lower radial force) over select diamond-shaped openings at a location on the heart valve prosthesis such that the segment(s) may better conform to the inner surface of the native valve annulus including any surface irregularities that may be present, thereby filling any gaps or cavities/crevices that may be present between the heart valve prosthesis and native tissue. Conversely, segments with less flexibility or conformability provide sufficient radial force to deploy the anti-paravalvular leakage component into apposition with the native valve annulus. Thus, the anti-paravalvular leakage component may be modified to have at least one segment having lower radial force and greater flexibility to better accommodate the surrounding native anatomy while maintaining high radial force and apposition in the rest of the anti-paravalvular leakage component. Stated another way, the anti-paravalvular leakage component may be considered to have regions or zones having greater flexibility and less radial force as compared to the rest of the anti-paravalvular leakage component. In addition, zones or sections of differing flexibility and radial force may be configured to minimize impingement of the conduction system. More particularly, the force exerted or applied by the segments may be varied to circumferentially to reduce the force applied to the vessel wall and thus minimize impingement of the conduction system.

Figure 34:
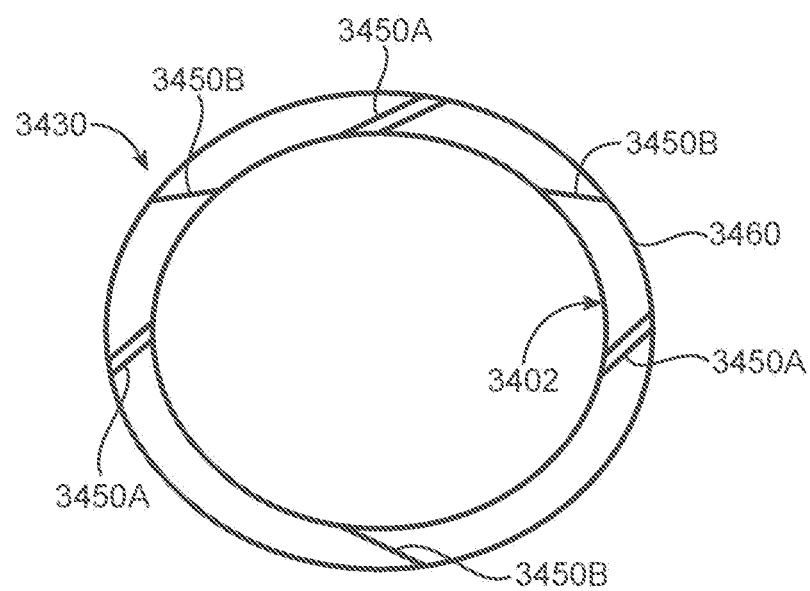
FIG. 34 is an end view of an anti-paravalvular leakage component coupled to a tubular stent according to an embodiment hereof, wherein the anti-paravalvular leakage component includes zones or sections of differing flexibility and radial force.

According to an embodiment hereof, in order to accomplish the zones or sections of differing flexibility and radial force, the number or frequency of self-expanding segments may be varied over select diamond-shaped openings at a location on the heart valve prosthesis corresponding to an area prone to leakage in situ. Conformability of the anti-paravalvular leakage component increases at the locations on the heart valve prosthesis having a higher or increased number of segments. In one embodiment hereof, the number or frequency of the segments is the highest at portions of the tubular stent that are prone to leakage in situ, such as adjacent to the native valve commissures or adjacent to areas having relatively greater levels of calcification. More particularly, as shown for example in FIG. 34, anti-paravalvular leakage component 3430 for a tubular stent 3402 that includes a plurality of oblique self-expanding segments 3450A, 3450B and an annular sealing element 3460 coupled to an outside surface of the segments. Segments 3450A are similar to segments 3150 described above in that two segments 3430A extend over a single diamond-shaped opening of tubular stent 3402, while segments 3450B are single segments extending over a single diamond-shaped opening of tubular stent 3402. In one embodiment hereof, segments 3450A are positioned or located at portions of tubular stent 3402 that are prone to leakage in situ, such as adjacent to the native valve commissures.

According to another embodiment hereof, the configurations of self-expanding segments may be varied in order to accomplish the zones or sections of differing flexibility and radial force. More particularly, various properties and/or designs of the self-expanding segments may be varied in order to selectively increase or decrease the flexibility or conformability of a particular segment. The plurality of segments may have different oblique angles, sizes or lengths, shapes or designs, and/or may be formed with different thicknesses in order to selectively increase or decrease the flexibility or conformability of a particular segment. For example, decreasing the angle of an oblique segment relative to the outer surface of the stent generally increases flexibility and conformability of the segment. In comparison, increasing the angle of an oblique segment results in less flexibility but greater radial force to ensure that the anti-paravalvular leakage component seals against the native anatomy. In another example, increasing the length of the segment generally increases flexibility and conformability of the segment. In comparison, shorter segments are less flexible but provide greater radial force. In another example, decreasing the thickness of the segment or a portion of the segment generally increases flexibility and conformability of the segment. In comparison, thicker segments are less flexible but provide greater radial force. In another example, material of the segment, i.e., spring steel verses Nitinol, may selectively impact the flexibility thereof. Other variations or modifications of the segments may be used to provide the anti-paravalvular leakage component with zones with different flexibilities, including but not limited to selecting any of the different shapes or designs of oblique segments described herein for its particular flexibility properties.

Figure 35:
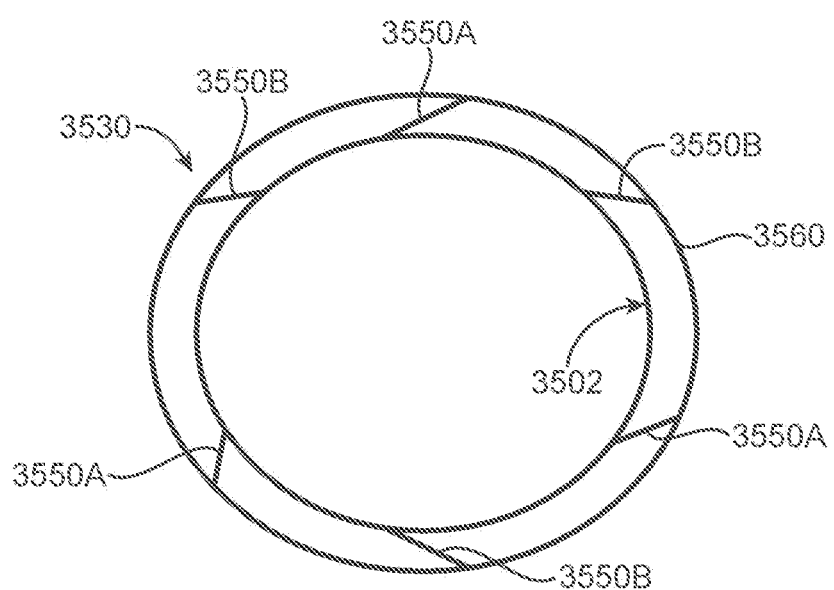
FIG. 35 is an end view of an anti-paravalvular leakage component coupled to a tubular stent according to another embodiment hereof, wherein the anti-paravalvular leakage component includes zones or sections of differing flexibility and radial force.

More particularly, as shown for example in FIG. 35, anti-paravalvular leakage component 3530 for a tubular stent 3502 that includes a plurality of oblique self-expanding segments 3550A, 3550B and an annular sealing element 3560 coupled to an outside surface of the segments. Segments 3550A are of a first configuration having a first flexibility or conformability, while segments 3550B are of a second configuration having a second flexibility or conformability that is different from the first flexibility. In one embodiment hereof, segments 3550A are more flexible than segments 3550B and are positioned or located at portions of tubular stent 3502 that are prone to leakage in situ, such as adjacent to the native valve commissures. As described above, one or more properties and/or designs such as the oblique angle, size or length, shape or design, and/or thickness of the self-expanding segments may be varied in order to selectively increase or decrease the flexibility or conformability of a particular segment. Although anti-paravalvular leakage component 3530 is shown with oblique self-expanding segments, one or more of the segments may be orthogonal to the tubular stent as described above with respect to segments 1250.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
    a stent having a proximal end, a distal end and a plurality of diamond-shaped openings, the stent having a compressed configuration for delivery within a vasculature and an expanded configuration for deployment within a native heart valve;
    a prosthetic valve component disposed within and secured to the stent; and
    an anti-paravalvular leakage component coupled to and encircling an outer surface of the stent, the anti-paravalvular leakage component including a plurality of self-expanding segments and an annular sealing element attached to the plurality of self-expanding segments,
    wherein each self-expanding segment has a first end and a second end that are attached directly to the outer surface of the stent at first and second attachment points, respectively,
    wherein the respective first and second attachment points are located on a portion of first and second diamond-shaped openings of the plurality of diamond-shaped openings such that the respective first and second attachment points are circumferentially spaced apart on the stent, the first and second diamond-shaped openings being directly adjacent to each other,
    wherein the anti-paravalvular leakage component has an expanded configuration in which an entire length of each self-expanding segment extends radially away from, and is oblique to, the outer surface of the stent, such that a plane defined by each self-expanding segment is non-perpendicular with respect to a tangential plane taken through its respective first and second attachment points on the stent.

2. The transcatheter valve prosthesis of claim 1, wherein each self-expanding segment has a concave profile when the anti-paravalvular leakage component is in the expanded configuration.

3. The transcatheter valve prosthesis of claim 1, wherein each self-expanding segment has a convex profile when the anti-paravalvular leakage component is in the expanded configuration.

4. The transcatheter valve prosthesis of claim 1, wherein the annular sealing element is attached to inner surfaces of the plurality of self-expanding segments and is disposed between the outer surface of the stent and the inner surfaces of the plurality of self-expanding segments when the anti-paravalvular leakage component is in the expanded configuration.

5. The transcatheter valve prosthesis of claim 1, wherein the annular sealing element is attached to outer surfaces of the plurality of self-expanding segments.

6. The transcatheter valve prosthesis of claim 1, wherein each self-expanding segment is U-shaped.

7. The transcatheter valve prosthesis of claim 1, wherein the plane defined by each self-expanding segment forms an angle between 20 and 80 degrees with respect to its respective tangential plane.

8. The transcatheter valve prosthesis of claim 1, wherein the respective first and second attachment points are located on side segments of the first and second diamond-shaped openings.

9. The transcatheter valve prosthesis of claim 1, wherein the respective first and second attachment points are located on peaks of the first and second diamond-shaped openings.

10. A transcatheter valve prosthesis comprising:
    a stent having a proximal end, a distal end and a plurality of diamond-shaped openings, the stent having a compressed configuration for delivery within a vasculature and an expanded configuration for deployment within a native heart valve;
    a prosthetic valve component disposed within and secured to the stent; and
    an anti-paravalvular leakage component coupled to and encircling an outer surface of the stent, the anti-paravalvular leakage component including a plurality of self-expanding segments and an annular sealing element attached to the plurality of self-expanding segments,
    wherein each self-expanding segment has a first end and a second end that are attached directly to the outer surface of the stent at first and second attachment points, respectively,
    wherein the respective first and second attachment points are located on a portion of first and second diamond-shaped openings of the plurality of diamond-shaped openings such that the respective first and second attachment points are circumferentially spaced apart on the stent, the first and second diamond-shaped openings being directly adjacent to each other,
    wherein the anti-paravalvular leakage component has an expanded configuration in which each self-expanding segment extends radially away from, and is oblique to, the outer surface of the stent, such that a plane defined by each self-expanding segment is non-perpendicular with respect to a tangential plane taken through its respective first and second attachment points on the stent, and
    wherein at least one self-expanding segment of the plurality of self-expanding segments includes only a middle U-shaped portion that extends radially away from the outer surface of the stent when the anti-paravalvular leakage component is in the expanded configuration.

11. The transcatheter valve prosthesis of claim 10, wherein the middle U-shaped portion is oriented to extend away from the first and second diamond-shaped openings.

12. The transcatheter valve prosthesis of claim 10, wherein the middle U-shaped portion is oriented to extend toward from the first and second diamond-shaped openings.

13. A transcatheter valve prosthesis comprising:
a stent having a proximal end, a distal end and a plurality of diamond-shaped openings, the stent having a compressed configuration for delivery within a vasculature and an expanded configuration for deployment within a native heart valve;
a prosthetic valve component disposed within and secured to the stent; and
an anti-paravalvular leakage component coupled to and encircling an outer surface of the stent, the anti-paravalvular leakage component including a plurality of self-expanding segments and an annular sealing element attached to the plurality of self-expanding segments,
wherein each self-expanding segment has a first end and a second end that are attached directly to the outer surface of the stent at first and second attachment points, respectively,
wherein the respective first and second attachment points are located on side segments or peaks of first and second diamond-shaped openings of the plurality of diamond-shaped openings such that the respective first and second attachment points are circumferentially spaced apart on the stent, the first and second diamond-shaped openings being directly adjacent to each other,
wherein the anti-paravalvular leakage component has an expanded configuration in which an entire length of each self-expanding segment extends radially away from, and is oblique to, the outer surface of the stent, such that a plane defined by each self-expanding segment is non-perpendicular with respect to a tangential plane taken through its respective first and second attachment points on the stent.

14. The transcatheter valve prosthesis of claim 13, wherein each self-expanding segment has a concave profile when the anti-paravalvular leakage component is in the expanded configuration.

15. The transcatheter valve prosthesis of claim 13, wherein each self-expanding segment has a convex profile when the anti-paravalvular leakage component is in the expanded configuration.

16. The transcatheter valve prosthesis of claim 13, wherein the annular sealing element is attached to inner surfaces of the plurality of self-expanding segments and is disposed between the outer surface of the stent and the inner surfaces of the plurality of self-expanding segments when the anti-paravalvular leakage component is in the expanded configuration.

17. The transcatheter valve prosthesis of claim 13, wherein the annular sealing element is attached to outer surfaces of the plurality of self-expanding segments.

18. The transcatheter valve prosthesis of claim 13, wherein each self-expanding segment is U-shaped.

19. The transcatheter valve prosthesis of claim 13, wherein the plane defined by each self-expanding segment forms an angle between 20 and 80 degrees with respect to its respective tangential plane.

\* \* \* \* \*